United States Patent
Zhang

(10) Patent No.: US 11,081,212 B2
(45) Date of Patent: Aug. 3, 2021

(54) SYSTEM AND METHOD FOR COMPUTING DRUG CONTROLLED RELEASE PERFORMANCE USING IMAGES

(71) Applicant: DigiM Solution LLC, Winchester, MA (US)

(72) Inventor: Shuang Zhang, Winchester, MA (US)

(73) Assignee: DigiM Solution LLC, Winchester, MA (US)

( * ) Notice: Subject to any disclaimer, the term of this patent is extended or adjusted under 35 U.S.C. 154(b) by 404 days.

(21) Appl. No.: 16/152,628

(22) Filed: Oct. 5, 2018

(65) Prior Publication Data

US 2019/0108322 A1 Apr. 11, 2019

Related U.S. Application Data

(60) Provisional application No. 62/569,021, filed on Oct. 6, 2017.

(51) Int. Cl.
*G06T 7/11* (2017.01)
*G06T 17/00* (2006.01)
(Continued)

(52) U.S. Cl.
CPC .............. *G16C 20/50* (2019.02); *G06F 30/23* (2020.01); *G06T 7/11* (2017.01); *G06T 17/00* (2013.01);
(Continued)

(58) Field of Classification Search
CPC . G06T 7/11; G06T 17/00; G06T 2207/20081; G06T 2210/41
(Continued)

(56) References Cited

U.S. PATENT DOCUMENTS 2,345,935 A 4/1944 Hassler
4,506,542 A 3/1985 Rose
(Continued)

OTHER PUBLICATIONS

Baish et al.; Role of Tumor Vascular Architecture in Nutrient and Drug Delivery: An Invasion Percolation-Based Network Model; 1996; Microvascular Research, vol. 51; pp. 327-346; Article No. 0031 (Year: 1996).*
(Continued)

*Primary Examiner* — David T Welch
(74) *Attorney, Agent, or Firm* — Hamilton, Brook, Smith & Reynolds, P.C.

(57) ABSTRACT

A method for computing the release rate of a controlled release drug and medical device using a combination of imaging data and computational physics is described. The method employs a three-dimensional digital representation of a drug sample, derived from two-dimensional or three-dimensional imaging, which captures the drug active pharmaceutical ingredient (API), excipients, and porosity with distinctive contrasts. Direct numerical simulations are conducted on the three-dimensional digital representation to derive effective transport properties of the API going through a porous matrix or membrane. Drug release rate can be predicted more efficiently than laboratory-based methods. When there is strong heterogeneity presented in the drug, a further method is described that engages imaging and release simulations at multiple scales. Computerized systems and programs for performing the methods are also described.

21 Claims, 14 Drawing Sheets

(51) Int. Cl.
    *G16C 20/50*     (2019.01)
    *G16H 50/50*     (2018.01)
    *G06F 30/23*     (2020.01)
    *G16C 20/70*     (2019.01)
    *G06F 111/10*     (2020.01)

(52) U.S. Cl.
    CPC ............ *G16C 20/70* (2019.02); *G16H 50/50* (2018.01); *G06F 2111/10* (2020.01); *G06T 2207/20081* (2013.01); *G06T 2210/41* (2013.01)

(58) Field of Classification Search
    USPC .......................................................... 703/2
    See application file for complete search history.

(56) References Cited

U.S. PATENT DOCUMENTS

| | | | |
|---|---|---|---|
| 8,377,499 | B2 | 2/2013 | Kleiner et al. |
| 8,389,044 | B2 | 3/2013 | Kleiner et al. |
| 8,628,568 | B2 | 1/2014 | Santos et al. |
| 8,637,111 | B2 | 1/2014 | Hsu et al. |
| 9,140,117 | B2 | 9/2015 | de Prisco |
| 9,183,326 | B2 | 11/2015 | de Prisco et al. |
| 2010/0108896 | A1* | 5/2010 | Surti .................. G01T 1/00 250/363.04 |
| 2012/0053918 | A1* | 3/2012 | Taylor .................... G16H 50/50 703/9 |
| 2015/0065803 | A1* | 3/2015 | Douglas ............. A61B 1/00045 600/200 |
| 2016/0066861 | A1* | 3/2016 | Taylor .................. A61B 5/0044 600/485 |
| 2017/0076062 | A1 | 3/2017 | Choi et al. |
| 2018/0049988 | A1* | 2/2018 | Chapanian ........... A61K 31/546 |
| 2019/0002282 | A1* | 1/2019 | Tamimi Marino ...... A61L 27/52 |
| 2019/0231697 | A1* | 8/2019 | Bellinger ............. A61K 9/2013 |
| 2019/0343190 | A1* | 11/2019 | Ogunbiyi ............... A61K 8/922 |
| 2020/0163642 | A1* | 5/2020 | Kinsey .................... A61B 6/461 |

OTHER PUBLICATIONS

Zhang et al.; Simulation of Drug Release from Biodegradeable Polymeric Microspheres with Bulk and Surface Erosions; 2003; Journal of Pharmaceutical Sciences; vol. 92, No. 10; pp. 2040-2056 (Year: 2003).*

Ahrenholz et al., Prediction of capillary hysteresis in a porous material using lattice-Boltzmann methods and comparison to experimental data and a morphological pore network model, Advances in Water Resources, vol. 31, 2008; pp. 1151-1173.

Blunt et al., "Pore-scale imaging and modelling," Advances in Water Resources, vol. 51, 2013; pp. 197-216.

Bondino et al., Relative permeabilities from simulation in 3D rock models and equivalent pore networks: critical review and way forward, International Symposium of the Society of Core Analysts held in Aberdeen, Scotland, UK, Aug. 27-30, 2012; 13 pages.

Brissos et al., "The role of long-acting injectable antipsychotics in schizophrenia: a critical appraisal," herapeutic Advances in Psychopharmacology, 2014, vol. 4[5], pp. 198-219.

Byrnes, "Reservoir Characteristics of Low-Permeability Sandstones in the Rocky Mountains," The Mountain Geologist, vol. 34, No. 1, Jan. 1997; pp. 39-51, The Rocky Mountain Association of Geologists.

Zhang, S., L. Canter & M. D. Sonnenfeld. Capillary Fluid Dynamics within Unconventional Rocks Investigated by Scanning Electron Microscopy, AAPG Bulletin, vol. 101, No. 11, 2017, pp. 1759-1765.

Dacy, "Core Tests for Relative Permeability of Unconventional Gas Reservoirs, SPE 1235427," Core Laboratories N. V., SPE Annual Technical Conference and Exhibition, Florence, Italy, Sep. 19-22, 2010, 18 pages.

DigiM Porosimetry Validation Page. http://www.digimsolution.com/products/image-simulation/porosimetry/, visited May 7, 2018, 5 pages.

D'Souza, "A Review of In Vitro Drug Release Test Methods for Nano-Sized Dosage Forms," Advances in Pharmaceutics vol. 2014, Nov. 20, 2014, Article ID 304757, 13 pages.

Fan et al., "The Issues and Challenges Involved in IVRT for Semi-solid Formulations", Drug Delivery Technology, Oct. 2007, vol. 7, No. 9, pp. 62-66.

Green et al., "Review of immobilized antimicrobial agents and methods for testing," Biointerphases, vol. 6, Issue 4, Dec. 2011, pp. MR13-MR28.

Hilpert et al., "Pore-morphology-based simulation of drainage in totally welling porous media," Advances in Water Resources, 24(3-4), pp. 243-255, 2001.

Joekar-Niasar et al., "Analysis of Fundamentals of Two-Phase Flow in Porous Media Using Dynamic Pore-Network Models: A Review," Critical Reviews in Environmental Science and Technology, 42:18, Dec. 30, 2015; pp. 1895-1976, DOI: 10.1080/10643389.2011.574101.

Landovitz et al., "The promise and Pitfalls of long-acting injectable agents for HIV prevention," Curr. Opin. HIV AIDS, 11(1), Jan. 2016, pp. 122-128.

Leu et al., "Fast X-ray Micro-Tomography of Multiphase Flow in Berea Sandstone: A Sensitivity Study on Image Processing," Transp. Porous Media 105, 2014, pp. 451-469. doi:10.1007/s11242-014-0378-4.

Markl et al., A Review of Disintegration Mechanisms and Measurement Techniques, Pharm Res. 2017, 34(5), pp. 890-917.

Naar et al., "Three-Phase Imbibition Relative Permeability," Society of Petroleum Engineers Journal, Dec. 1961, 5 pages.

Putz et al., "Microscopy Supported Multi-scale Modeling of PEM Fuel Cells," Presentation at 231st Electrochemical Society Meeting, session F03:Multiscale Modeling, Simulation and Design, New Orleans, May 28-Jun. 1, 2017, 3 pages.

Saraf et al., Three-phase relative permeability measurement using a nuclear magnetic resonance technique for estimating fluid saturations, Society of Petroleum Engineers Journal, Sep. 1967). retrieved from the Internet at https://www.onepetro.org/journal-paper/SPE-1760-PA; 8 pages.

Shikhov et al., "Evaluation of Capillary Pressure Methods via Digital Rock Simulations," Transp Porous Media, vol. 107, 2015, pp. 623-640.

Siepmann et al., "Fundamentals and Applications of Controlled Release Drug Delivery," Springer, 2012. Ebook: https://www.springer.com/gp/book/9781461408802.

Versteeg et al., "An introduction to computational fluid dynamics," The finite volume method (2 Edition). Pearson Education Limited, 2007, 577 pages.

Wu et al., "Microimaging Characterization and Release Prediction of Controlled Release Microspheres," 18-A-137-CRS. Controlled Release Society Annual Meeting and Exposition, New York City, New York, U.S.A. Jul. 22-24, 2018; 1 page.

Zhang et al., "Porosity and permeability analysis on nanoscale FIB-SEM tomography of shale rock," Society of Core Analysis 2011 Symposium, paper A080, Austin, Texas, Sep. 18-21, 2011, 12 pages.

Zhang et al., "Micron to millimeter upscale of shale rock properties based on three-dimensional imaging and modeling," Society of Core Analysis 2012 Meeting, paper A080, Aberdeen, UK, Aug. 26-31, 2012, 12 pages.

Zhang, "Artificial Intelligence Image Processing," DigiM Technology Highlight 2017, Jul. Issue, Jul. 29, 2017, 8 pages.

Zhang et al., "Quantitative Characterization of Crystallization in Amorphous Solid Dispersion Drug Tablets Using X-Ray Micro-Computed Tomography," Microscopy & Microanalysis 2018, Baltimore, Maryland, Aug. 5-9, 2018, 2 pages.

Zhang et al., "Reconstruction of Three-Dimensional Micro-Structures From Two-Dimensional Microscopic Images Using Texture Synthesis and Phase Field Method," Poster ID PDP-54, date unknown.

Byrnes et al., "Effect of pressure and water saturation on the permeability of western tight sandstones," 1979, Proc. 5th Annual

(56) References Cited

OTHER PUBLICATIONS

DOE Symposium Enhanced Oil and Gas Recovery, Aug. 22-26, Tulsa, OK, p. 231-246, L-5/1 to L-5/16.
Baxter, JL, Kukura J, Muzzio FJ. Hydrodynamics-induced variability in the USP apparatus II dissolution test. Int J Pharm 2005;292:17-28.
Byrnes et al., "Application of integrated core and 3D image rock physics to characterize Niobrara chalk properties including relative permeability with bound water effect," Unconventional Resources Technology Conference, URTeC 2670963, Austin, Texas, USA, Jul. 24-26, 2017.
Pancholi, "A review of imaging methods for measuring drug release at nanometre scale: a case for drug delivery systems," Expert Opinion on Drug Delivery. vol. 9, 2012, Issue 2.
Zhang et al., "DigiMedicine: FIB-SEM/MicroCT three-dimensional imaging for drug microstructure and deliverability characterization," AAPS National Biotechnology Conference 2016, 1 page.
Zhang et al., "Microscopic Image Based Drug Delivery System Characterization," AAPS 2016 Annual Conference, Poster #02W0900, Denver, CO, USA, Nov. 13-17, 2017.
Khalili et al, "Permeability Upscaling for Carbonates from the Pore-Scale Using Multi-Scale X-Ray-CT Images,", 2013, SPE Reserv. Eval. Eng. 16, 353-368. doi:10.2118/152640-MS.
Diez-Escudero, A., Espanol M, Montufar EB, Di Pompo G, Ciapetti G, Baldini N, Ginebra MP. Focus Ion Beam/Scanning Electron Microscopy Characterization of Osteoclastic Resorption of Calcium Phosphate Substrates. Tissue Eng Part C Methods. Feb. 2017;23(2):118-124. doi: 10.1089/ten.TEC.2016.0361. Epub Feb. 3, 2017.
Fenwick et al., "Network Modeling of Three-Phase Flow in Porous Media," SPE Journal, Mar. 1998, 12 pages.
Grimaldi-Bensouda, L. et al., Does long-acting injectable risperdone make a difference to the real life treatment of schizophrenia? Results of the cohort for the general study of Schizophrenia (CGS), Schizophrenia Research, 134 (2012) 187-194.
Hill, R. (1963), "Elastic properties of reinforced solids: some theoretical principles." Journal of the Mechanics and Physics of Solids, 11 (5): 357-372.
Zhang, S., Correlative focused ion beam scanning electron microscope and x-ray micro-computed tomography imaging on multi-scale drug release characterization and three-dimensional-printing manufacturing. CRS 2017 Annual Conference Poster Presentation. Poster No. 128, Jul. 16-19, 2017, Boston.
Pisano, Roberto, Antonello A. Barresi, Luigi C. Capozzi, Giorgia Novajra, Irene Oddone, and Chiara Vitale-Brovarone. Characterization of the mass transfer of lyophilized products based on X-ray micro-computed tomography images. Drying Technology, vol. 35, No. 8., 933-938, 2017.
Qureshi SA, McGilveray IJ. Typical variability in drug dissolution testing: Study with USP and FDA calibrator tablets and a marketed drug (glibenclamide) product. Eur J Pharm Sci 1999;7:249-258.
Siepmann, et al., "Modeling of diffusion controlled drug delivery," J Control Release. Jul. 20, 2012;161(2):351-62. doi: 10.1016/j.jconrel.2011.10.006. Epub Oct. 13, 2011.
Wang et al., "Micro-CT analysis of matrix-type drug delivery devices and correlation with protein release behaviour," J Pharm Sci. Jun. 2010;99(6):2854-62. doi: 10.1002/jps.22027.
Byrnes et al., "Comparison of Core Petrophysical Properties Between Low-Permeability Sandstone Reservoirs: Eastern U.S. Medina Group and Western U.S. Mesaverde Group and Frontier Formation," SPE 60304 proceedings of the 2000 SPE Rocky Mountain Regional/Low Permeability Reservoirs Symposium held in Denver, CO, Mar. 12-15, 2000, p. 10.
Byrnes et al., "Issued With Gas and Water Relative Permeability in Low-Permeability Sandstones," AAPG Hedberg Conference, Understanding, Exploring and Developing Tight Gas Sands, Apr. 24-29, 2005.
Castle et al., "Petrophysics of Lower Silurian sandstones and integration with the tectonic-stratigraphic framework, Appalachian basin, United States," AAPG Bulletin, vol. 89, No. 1, Jan. 2005, pp. 41-60.
Jones et al, 1980, A laboratory study of low-permeability gas sands: paper SPE 7551-PA, Journal of Petroleum Technology, v. 32, No. 9, p. 1631-1640. DOI: 10.2118/7551-PA.
Rose, W., "Some Problems in Applying the Hassler Relative Permeability Method," 32 J. Petroleum Technology, 1161-63 (Jul. 1980).
Davis Yohanes Arifin et al., "Mathematical modeling and simulation of drug release from microspheres: Implications to drug delivery systems", Advanced Drug Delivery Reviews, vol. 58, No. 12-13, Nov. 1, 2006, pp. 1274-1325.
International Search Report and Written Opinion for International Application No. PCT/US2018/054546, entitled: "System and Method for Computing Drug Controlled Release Performance Using Images", dated Mar. 22, 2019.
Kanckstedt, M. a., Sheppard, a. P., Sahimi, M., 2001. Pore network modelling of two-phase flow in porous rock: The effect of correlated heterogeneity. Adv. Water Resour. 24, 257-277. doi:10.1016/S0309-1708(00)00057-9.
Lahiri, Arka, Chandrashekhar Tiwary, Kamanio Chattopadhyay, Abhik Choudhury, Eutectic colony formation in systems with interfacial energy anisotropy: A phase field study, Computational Materials Science, Volume 130, Apr. 1, 2017, pp. 109-120.
Olsen et al., Two-fluid Flow in Sedimentary Rock: Simulation, Transport and Complexity, J. Fluid Mechanics, vol. 341, 1997, pp. 343-370.
Whitaker, "The Method of Volume Averaging," Kulver Academic Publishers, EBook, 1999, 236 pages.
Rivas-Gomez, S. et al., "Numerical Simulation of Oil Displacement by Water in a Vuggy Fractured Porous Medium," Society of Petroleum Engineers, Feb. 11, 2001-Feb. 14, 2001, SPE 66386, pp. 1-9.
Byrnes, A.P., Cluff, R.C., and Webb, J.C., 2009, Analysis of Critical Permeability, Capillary and Electrical Properties for Mesaverde Tight Gas Sandstones from Western U.S. Basins, U.S. Department of Energy Final Technical Report for Project #DE-FC26-05NT42660, DOI 10.2172/971248, 248 pgs.—https://www.osti.gov/servlets/purl/971248.
Byrnes, "Permeability, Capillary Pressure, and Relative Permeability Properties in Low-Permeability Reservoirs and the Influence of Thin, High-Permeability Beds on Production," Gas in Low Permeability Reservoirs of the Rocky Mountain Region, The Rocky Mountain Association of Geologists, 2005, p. 69-108.
Canter, et al, "Primary and Secondary Organic Matter Habit in Unconventional Reservoirs," in T. Olson, ed., Imaging Unconventional Reservoir Pore Systems: AAPG Memoir 112, 2016, p. 9-24.
Heiba, A.A., Davis, H.T., and Scriven, L.E., 1984, Statistical network theory of three-phase relative permeabilities, SPE/DOE #12690, SPE/DOE Fourth Symposium on Enhanced Oil Recovery, Tulsa, OK, Apr. 15-18, 1984, p. 121-134.
International Preliminary Report on Patentability for Application No. PCT/US2018/054546, entitled "System and Method for Computing Drug Controlled Release Performance Using Images" dated Apr. 8, 2020.

* cited by examiner

10μm

SYSTEM AND METHOD FOR COMPUTING DRUG CONTROLLED RELEASE PERFORMANCE USING IMAGES

RELATED APPLICATION

This application claims the benefit of U.S. Provisional Application No. 62/569,021, filed on Oct. 6, 2017. The entire teachings of the above application are incorporated herein by reference.

BACKGROUND

Release rate is used to quantify the amount, and speed, of the active pharmaceutical ingredient (API) released from a drug product to a patient's body. As the most important part of a drug release kinetics matrix, a drug release rate provides critical information about dosage form behavior and is a key parameter used to assess product safety and efficacy. A drug release rate depends on the release control mechanism, drug solubility, drug loading, and fluid properties of the release site of the specific patient. Modern drug designs employ increasingly complex release control mechanisms, which are further categorized as immediate release, pulse release, modified release, delayed release, and extended release. The latter four scenarios are often generalized as controlled release, which might engage a porous media. A porous media provides supreme release control through its porosity, pore distribution, pore space tortuosity, and pore wall surface properties. In addition to the release retardation designs, such as a membrane or a matrix, sophisticated controlled release behavior, such as osmotic pumping and particle surface engineering, are actively researched and applied [Siepmann et. al., 2012]. Patents have been filed on the design of controlled drug release. For example, in [U.S. Pat. No. 8,637,111, Methods for modulating the release rate of a drug-coated stent, 2012] and [U.S. Pat. No. 8,628,568, Stent with drug coating with variable release rate, 2010], methods for modulating the release rate of a drug coated stent with either a hydrophilic polymer or a geometry of a strut network are described. [U.S. Pat. No. 8,389,044, Poly(ester amide)-based drug delivery systems with controlled release rate and morphology, 2011] and [U.S. Pat. No. 8,377,499, Methods of forming Poly(ester amide)-based drug delivery systems with controlled release rate and morphology] describe a general method of polymer coating a medical device.

In order to achieve sophisticated controlled release designs, release rate is a performance measure that is important from both characterization and design evaluation standpoints. Tremendous in-vitro and in-vivo experiments have to be conducted on a large range of design parameters to make sure that the release rate is reproducibly honoring the designed disease-treatment purpose of the specific drug. For example, in a controlled release membrane design, a water soluble polymer and a water insoluble polymer are mixed in an organic solvent. After they are spray-dried to a drug sample, an enteric coating is formulated. The coating will protect the drug API during transportation, pharmacy shelving, and patient home storage. When the coated drug is ingested by a patient, the coating comes in contact with a body fluid environment. The water soluble polymer will be dissolved, and the porous media of the water insoluble polymer is formed. The thickness of the coating and the volume fraction of the water soluble polymer dictates when the drug will start to release. Once the drug has passed the acidic stomach environment, it will begin to release the API in the patient's intestinal environment. The porosity, pore distribution, and pore tortuosity formed by the water-soluble polymer, will subsequently determine the release rate of the drug. A 10% decrease in alcohol content used in the organic solvent can change an 8-hour controlled release drug pellet design to a 30-minute immediate release drug pellet design [S. Zhang, C. Zhang, G. Byrnes. Microscopic Image Based Drug Delivery System Characterization. AAPS 2016 Annual Conference, Poster #02W0900, Denver, Colo., USA, Nov. 13-17, 2017]. In addition to alcohol content in the organic solvent, other compositions in the solvent, spray-drying temperatures, droplet size distributions, polymer types, polymer grades and polymer degradation profiles are other parameters exemplifies the large parameter space that need to be evaluated during controlled release design.

A controlled release design is conventionally tested in-vitro and in-vivo. In-vitro drug release testing measures the release of the API from the drug product matrix in a controlled laboratory environment. It involves subjecting the drug dosage form to a set of conditions that will induce drug release and quantify the amount of the drug released under those conditions. In the development phase, in-vitro drug release testing is used to assess differences between design prototypes, in predicting the timeframe of the API release, and in modeling in-vivo behavior. Conventional methods to categorize in-vitro physical measurements includes dissolution testing, in vitro release testing, and elution testing. These physical measurement methods are briefly described below, followed by their limitations in modern controlled release design.

In-vitro dissolution testing of oral dosage forms measures the dissolution rate of an amount of a drug substance going from a solid state into a solution per unit time under standardized conditions. The goals of a dissolution test include: prediction of bioavailability (a surrogate parameter of the therapeutic efficacy), indication of the robustness of the dosage form (drug product safety), and implication of variations in the manufacturing process (which may have a critical influence on performance). Nomenclature for the compendial apparatus for dissolution testing includes USP 1 baskets, USP 2 paddles, USP 3 reciprocating cylinders, USP 4 flow-through cell, USP 5 paddle over disk, USP 6 cylinders and USP 7 reciprocating holders [Hanson, R.; Gray, V. Handbook of Dissolution Testing, 3rd ed.; Dissolution Technologies, Inc.: Hockessin, D E, 2004; p 25.].

In-vitro release of the API from topical and transdermal products, and subsequent permeation through a membrane, can be tested in a vertical diffusion cell (i.e. Franz diffusion cell). In this apparatus, formulation is applied to, or put in contact with, a membrane that is in contact with a receiving medium. The receiving medium is sampled as a function of time and the API is quantitated to determine a permeation/flux profile. The membrane materials include the synthetic polymer, cadaver or animal skin, and tissue constructs. The choice of membrane is dependent upon the purpose of the test (i.e. development vs. quality control) and the robustness of the model. This technique is applicable not only to externally applied topical formulations, but also to products that deliver via the vaginal, rectal, buccal, or nasal routes. [Fan Q, Mitchnick M, Loxley A, "The Issues and Challenges Involved in IVRT for Semi-solid Formulations", Drug Delivery Technology, 2007: 7: 62-66.]

The release of a drug from an implantable device can be assessed by subjecting the device to being soaked or stirred into a suitable medium, usually with episodic medium exchange. The medium is sampled periodically for quantitation to establish an elution profile. Elution testing can be performed with set periodic medium exchanges (i.e. daily) or with medium circulating around/through the device (i.e. flow-through apparatus). The choice of medium, test volumes, and exchange frequency depend on the nature of the device. The conditions used for elution are dependent upon the purpose of the test, while simulant conditions are used primarily during development, and more robust sink conditions are used as quality control tests. [John-Bruce D. Green, Timothy Fulghum, Mark A. Nordhaus. A review of immobilized antimicrobial agents and methods for testing, *Biointerphases*, December 2011, Volume 6, Issue 4, pp MR13-MR28].

When a drug dosage form is engineered with nanoparticles, sample and separate, continuous flow, and dialysis membrane methods, or some combination, are used. [Susan D'Souza, A Review of In Vitro Drug Release Test Methods for Nano-Sized Dosage Forms, Advances in Pharmaceutics Volume 2014 (2014), Article D 304757].

While these experimental techniques can be rigorously designed and progressively improved, the drug has to be physically released from the sample. Serious concerns and problems are reported in the literature [Baxter J L, Kukura J, Muzzio F J. Hydrodynamics-induced variability in the USP apparatus II dissolution test. Int J Pharm 2005; 292: 17-28.] [Qureshi S A, McGilveray I J. Typical variability in drug dissolution testing: Study with USP and FDA calibrator tablets and a marketed drug (glibenclamide) product. Eur J Pharm Sci 1999; 7:249-258.]. These reported problems often relate to: (1) failing of the performance evaluations of the apparatuses (calibration) and/or products; (2) lack of establishing the link between in-vitro dissolution results and in-vivo results, commonly referred to as in-vitro-in-vivo correlations or IVIVC; (3) lack of objectivity in setting or selecting experimental conditions for product evaluations; and (4) setting unreasonably wide tolerances based on complex and convoluted rationales. For a drug with a longer designed release time, the physical measurement process is time consuming. Furthermore, rigorous tests typically require studying a large number of samples in a controlled manner, hence are lengthy and resource consuming. Exploring a large parameter space with an experimental method is also risky as an optimal design interval can be missed.

Imaging has been used quite extensively in the pharmaceutical industry. A dominant imaging effort is seen in translational imaging [Ketan Pancholi. A review of imaging methods for measuring drug release at nanometre scale: a case for drug delivery systems. Expert Opinion on Drug Delivery. Volume 9, 2012, Issue 2.]. Biomarkers are typically used when a resolution is in the order of 100s of microns. Ultra-violet (UV) imaging, sometimes in combination with Raman spectroscopy and the channel flow cell method, provides temporarily and spatially resolved absorbance maps. Imaging is also reported to serve as a promising technique for the study of the immediate release formulation with disintegration [Daniel Markl and J. Axel Zeitler. A Review of Disintegration Mechanisms and Measurement Techniques, *Pharm Res.* 2017; 34(5): 890-917]. Higher resolution imaging work, on drug products, as a qualitative drug characterization tool, is reported using Micro-Computed Tomography (MicroCT) [Wang et. al., 2010. *J Pharm Sci.* 2010 June; 99(6):2854-62.] or Focused Ion Beam Scanning Electron Microscopy (FIB-SEM) [Diez-Escudero et. al., *Tissue Eng Part C Methods.* 2017 February; 23(2):118-124.]. More recently, image-based quantification has gained a lot of attention [Shawn Zhang, Joseph Neilly, Aiden Zhu, Jacie Chen, Gerald Danzer. Quantitative Characterization of Crystallization in Amorphous Solid Dispersion Drug Tablets Using X-Ray Micro-Computed Tomography. Microscopy & Microanalysis 2018, Baltimore, Md., Aug. 5-9, 2018.] [Dan Wu and Shawn Zhang. Microimaging Characterization and Release Prediction of Controlled Release Microspheres. 18-A-137-CRS. Controlled Release Society Annual Meeting and Exposition, New York City, N.Y., U.S.A. Jul. 22-24, 2018.] [S. Zhang. Correlative focused ion beam scanning electron microscope and x-ray micro-computed tomography imaging on multi-scale drug release characterization and three-dimensional-printing manufacturing. CRS 2017 Annual Conference Poster Presentation. Poster No. 128, Jul. 16-19, 2017, Boston.] [S. Zhang & J. Chen. DigiMedicine: FIB-SEM/MicroCT three-dimensional imaging for drug microstructure and deliverability characterization. AAPS National Biotechnology Conference 2016.], but image-based drug release simulation work remains sparse.

Conventional release rate modeling is mostly theoretical or empirical. The Diffusion Layer Model (DLM) assumes that a layer of liquid, H cm thick, adjacent to the solid surface remains stagnant as the bulk liquid passes over the surface with a certain velocity. The reaction at the solid/liquid interface is assumed to be instantaneous forming a saturated solution, Cs, of the solid in the static liquid film. The rate of dissolution is governed entirely by the diffusion of the solid molecules from the static liquid film to the bulk liquid according to Fick's first law:

$$\vec{J} = -D\vec{\nabla}c$$

where $\vec{J}$ is the amount of substance passing perpendicularly through a unit surface area per time, D is a diffusion coefficient and $\vec{\nabla}c$ is concentration gradient. After time t, the concentration at the boundary between the static liquid layer and the bulk liquid, becomes Ct. Once the solid molecules pass into the bulk liquid, it is assumed that there is rapid mixing and the concentration gradient disappears. The theory predicts that if the concentration gradient is always constant, i.e. C s–C t is constant because C s>>C t ("sink" conditions which usually mean C s>10 C t), then a uniform rate of dissolution is obtained. In controlled release designs, an interfacial barrier model is often used to modulate the reaction at the solid/liquid interface. The interfacial barrier is either porous initially, or becomes porous during the release. Hence, the dissolution of a drug is not instantaneous due to the high-activation, free-energy barrier which has to be surmounted before the solid could be dissolved. The rate of diffusion in the static layer is relatively fast in comparison to the surmounting of the energy barrier, which therefore becomes rate limiting factor in the dissolution process. The diffusion layer model is the most commonly used with various alterations [Siepmann J., Siepmann F. Modeling of diffusion controlled drug delivery, J Control Release. 2012 Jul. 20; 161(2):351-62. doi: 10.1016/j.j conrel.2011.10.006. Epub 2011 Oct. 13.], controlled release through a porous release barrier is poorly studied and rarely reported. Porosity, pore size distribution, pore connectivity, pore throat, and matrix surface properties influence release rate and complicate its modeling. [Roberto Pisano, Antonello A. Barresi, Luigi C. Capozzi, Giorgia Novajra, Irene Oddone, and Chiara Vitale-Brovarone. Characterization of the mass transfer of lyophilized products based on X-ray micro-computed tomography images. Drying Technology, VOL. 35, No. 8., 933-938, 2017] correlated porous microstructure of a lyophilized solid with the sublimation rate, where average pore size is used to derive the effective diffusivity coefficient through an empirical relationship.

In other application fields, particularly material science [A. Putz, J. Jankovic, S. Zhang, D. Susac, M. Secanell, M. Sabharwal. Microscope Supported Multi-scale Modeling of PEM Fuel Cell. Presentation at 231st The Electrochemical Society Meeting, session F03: Multiscale Modeling, Simulation and Design, New Orleans, May 28-Jun. 1, 2017.] and geoscience [Ian P. Byrnes, Shawn Zhang, Lyn Canter, Mark D. Sonnenfeld. Application of Integrated Core and Multi-scale 3-D Image Rock Physics to Characterize Porosity, Permeability, Capillary Pressure, and Two- and Three-Phase Relative Permeability in the Codell Sandstone, Denver Basin, Colo. Unconventional Resources Technology Conference, URTeC 2901840, Houston, Tex., USA, 23-25 Jul. 2018.][S. Zhang, Robert E. Klimentidis, & Patrick Barthelemy. "Micron to millimeter upscale of shale rock properties based on three-dimensional imaging and modeling." *Society of Core Analysis* 2012 *Meeting*, paper A080, Aberdeen, UK, Aug. 26-31, 2012.], image-based computation method is of growing importance for its similar advantages over physical measurements.

SUMMARY

An embodiment according to the invention relates to a method which evaluates and predicts the active pharmaceutical ingredient release rate for a controlled release drug or medical devices. The release rate computed, in accordance with an embodiment of the invention, can be used in many areas such as drug design optimization, precision medicine development, and cancer treatment evaluation. Transport properties other than release rate can also be computed in a similar manner with applications in material science and geoscience. An embodiment according to the invention also relates to a computer system, and components thereof, for performing such a method.

A feature of an embodiment according to the invention is a method for calculating the release rate of a drug or medical device by combining experimental data (images, in this embodiment) with numerical simulation.

A further feature of an embodiment according to the invention is a system for computing release rate on the said images. Said system has imaging capability to capture the microstructure of the drug release system with appropriate resolution and contrast, computing capability to process these images and compute the release rate, storage capability to host and provide access to the imaging and derived data, and a graphical user interface to allow the user to have control over the data and the process.

Another feature of an embodiment according to the invention is a computer program product on a computer readable medium that, when performed on an operating system in a computerized device, provides a method for performing one or more or all of the indicated computations.

A further feature of an embodiment according to the invention is a method, and/or system, of using the prediction of the calculated release rate to evaluate the performance of a drug, or a medical device, with various controlled release designs or with mass transport through any porous media.

To achieve these and other advantages and, in accordance with the purpose of the present invention, as embodied and broadly described herein, an embodiment according to the invention relates, in part, to the following steps:

1. Imaging is conducted on a representative drug sample that is subjected to a release evaluation, where, 1.1 The imaging devices can be computed tomography (CT or MicroCT), focused ion beam scanning electron microscopy (FIB-SEM), magnetic resonance imaging (MRI), ultrasound imaging (UAI), light microscopy (LM), transmission electron microscopy (TEM), Raman Imaging (RI), atomic force microscopy (AFM), or any imaging method at an appropriate resolution.

1.2 Sample representativeness on the collected image is critically evaluated.

1.3 The drug sample can be drug (including but not limited to tablet, pellet, spray-dried particle, lyophilized solid, micro- and nano-spheres, implant), medical device, drug/device combination, biological tissue, or any material sample where one or multiple substances transport through a porous media to the target site during its partial or complete life time.

1.4 The release evaluation can be extended release, pulse release, immediate release, delayed modified release, controlled release, or a combination of any release.

2. A three-dimensional digital representation of the drug and its release system is reconstructed from the said images, where, 2.1 The three-dimensional digital representation can be segmented from three-dimensional images, reconstructed from one or multiple two-dimensional images in combination with micro-structure modeling, or numerically generated using previously analyzed and validated three-dimensional digital representations of other samples.

2.2 The image segmentation, when needed, is conducted using either artificial intelligence, conventional intensity-threshold algorithms, intensity-gradient algorithms, or any image segmentation algorithms.

2.3 The three-dimensional digital representation reconstructed from two-dimensional images, when needed, uses either the grayscale or segmented binary images.

3. The simulation of the drug release quantity is conducted with the previously stated three-dimensional digital representation using the connectivity of a percolating network of porosity or the drug API phase which releases and forms a percolating network of porosity.

4. One or multiple direct numerical simulations on physical properties governing the release mechanism of the said drug sample is conducted on the said three-dimensional digital representation, where, 4.1 The partial differential equations governing physical properties solved numerically includes, 4.1.1 Second Fick's law for diffusion 4.1.2 Naiver-Stokes equations for pressure gradient or flux driven flow 4.1.3 Ohm's law for electrical conductivity 4.1.4 Fourier's law for thermal conductivity 4.2 The voxels from three-dimensional digital representation are used directly as computational cells or elements.

4.3 The numerical schemes can be finite volume, finite difference, finite element, Lattice Boltzmann or others.

4.4 The simulation of physical properties are conducted on various release stages as shown in Feature #3.

5. Optionally, when strong heterogeneity is presented in the drug sample, a multi-scale approach is engaged where, 5.1 Additional simulations on multiple three-dimensional digital representations at different scales are performed to solve physical properties at different scales.

5.2 Physical properties at a higher resolution (hence, a smaller sample size) are integrated with the previously stated simulation results (Feature #4).

6. Derive the time of release using three-dimensional digital representation of the drug, physical properties of the drug, and an established release model, where, 6.1 The physical properties are most often the effective diffusivity coefficient, permeability, or others.

6.2 The established release models are the Higuchi thin plate model, Higuchi cylinder model, Higuchi sphere model or others depending on the drug sample geometry and the designed release physics.

6.3 Optionally, when Feature 5 is necessary, the release model will be modified with the multi-scale factor derived from both high-resolution three-dimensional digital representation and low-resolution three-dimensional digital representation.

7. Optionally, modify the three-dimensional digital representation of the drug release system and repeat features #2-#6 with one or multiple iterations to achieve a specific release profile.

8. A system for performing the steps described in the previous features comprises, 8.1 A computing hardware with single or multiple central processing units (CPUs) that can conduct the above said image processing and simulations.

8.2 A storage hardware with single or multiple hard disks (HD) that can store, with redundancy, all the resulting data.

8.3 A graphical user interface (GUI) with desktop, web-based cloud, or hybrid implementations that allows the user to control, manipulate, and access the system.

8.4 An image processing and numerical simulation software.

In accordance with an embodiment of the invention, there is provided an image-based, computer-implemented method of predicting a release rate of a pharmaceutical ingredient from a release system. The method comprises constructing a three-dimensional digital representation of the release system based on physical imaging data of a sample of the release system. The three-dimensional digital representation satisfies a representative elementary volume evaluation of the pharmaceutical ingredient in the release system. The release of the pharmaceutical ingredient from the release system is computationally simulated based on physical properties governing the release and on the three-dimensional digital representation of the release system. The computational simulation is further based on at least one of: (i) a percolating network of porosity of the release system, and (ii) a percolating network of porosity formed as the pharmaceutical ingredient is released from the release system.

In further, related embodiments, constructing the three-dimensional digital representation may comprise, for at least one iteration: determining whether the three-dimensional digital representation of the release system satisfies the representative elementary volume evaluation; and, if the three-dimensional digital representation of the release system does not satisfy the representative elementary volume evaluation, revising the three-dimensional digital representation of the release system and again determining whether the three-dimensional digital representation of the release system satisfies the representative elementary volume evaluation. Constructing the three-dimensional digital representation may comprise, for at least one iteration: determining whether the three-dimensional digital representation of the release system satisfies the representative elementary volume evaluation; and, if the three-dimensional digital representation of the release system does not satisfy the representative elementary volume evaluation, using revised physical imaging data of a sample of the release system as the basis of the three-dimensional digital representation of the release system and again determining whether the three-dimensional digital representation of the release system satisfies the representative elementary volume evaluation. The physical imaging data of the sample of the release system may comprise three-dimensional imaging data. The physical imaging data of the sample of the release system may comprise two-dimensional imaging data. The method may comprise constructing the three-dimensional digital representation of the release system based on at least one pre-existing three-dimensional digital representation of a release system with identical or similar design.

In other related embodiments, constructing the three-dimensional digital representation of the release system may comprise performing image segmentation of the physical imaging data to identify material phases in the physical imaging data. Performing the image segmentation may comprise performing at least one of: an intensity-based image segmentation and a gradient-based image segmentation. Performing the image segmentation may comprise using an artificial intelligence-based image segmentation. Using the artificial intelligence-based image segmentation may comprise using a human-trained image segmentation logic module to recognize image features. Constructing the three-dimensional digital representation of the release system may comprise: processing the physical imaging data to produce pre-processed physical imaging data by performing at least one of: removal or reduction of imaging artifacts, calibration of imaging contrast, and enhancement of image features; performing image segmentation of the pre-processed physical imaging data to identify material phases in the physical imaging data, thereby producing segmented image data; and performing microstructure post-processing of the segmented image data.

In further related embodiments, computationally simulating the release of the pharmaceutical ingredient from the release system may comprise at least one of: performing an empirical-based release simulation; performing a reduced order geometry-based release simulation; performing a geometry-based release simulation; and performing a voxel-based release simulation. Computationally simulating the release of the pharmaceutical ingredient from the release system may comprise performing a percolation-based simulation to determine a non-dimensional release profile comprising an amount of pharmaceutical ingredient released at each simulated non-dimensional step of a layer by layer release of the pharmaceutical ingredient proceeding from an exterior surface of the release system to an interior surface of the release system. Computationally simulating the release of the pharmaceutical ingredient from the release system may comprise performing a percolation-based simulation to determine an intermediate release stage microstructure for each simulated non-dimensional step of a layer by layer release of the pharmaceutical ingredient from the release system, the layer by layer release proceeding from an exterior surface of the release system to an interior surface of the release system. Each intermediate release stage microstructure may comprise an amount of pharmaceutical ingredient remaining, an amount of pharmaceutical ingredient released to produce porous volume, and an infinitesimal layer of pharmaceutical ingredient currently being released at the intermediate release stage. The method may further comprise using the determined intermediate release stage microstructures to determine an effective diffusivity coefficient. The method may comprise determining concentration distribution of the pharmaceutical ingredient throughout the percolating network of porosity based on solving flux balance with a finite volume method; and, based on the concentration distribution, determining the effective diffusivity coefficient. The method may comprise determining the effective diffusivity coefficient based on direct numerical simulation employing voxels of the three-dimensional digital representation of the release system as a smallest computation cell of the direct numerical simulation. The method may comprise predicting the release rate of the pharmaceutical ingredient from the release system based on at least: (i) a non-dimensional release profile and (ii) the effective diffusivity coefficient.

In other related embodiments, the method may comprise performing a first simulation based on physical imaging data obtained at a first resolution scale; and performing a second simulation based on physical imaging data obtained at a second resolution scale, different from the first resolution scale. The first simulation may comprise a percolation-based simulation based on physical imaging data obtained at the first resolution scale; and the second simulation may comprise an effective diffusivity simulation based on physical imaging data obtained at the second resolution scale. The physical imaging data may comprise images produced from at least one of: computed tomography; focused ion beam scanning electron microscopy; magnetic resonance imaging; ultrasound imaging; light microscopy; transmission electron microscopy; Raman Imaging; and atomic force microscopy. The release system may comprise at least one of: a drug; a medical device; and biological tissue. The drug may comprise at least one of: a tablet; a pellet; a spray-dried particle; a lyophilized solid; a micro-sphere; a nano-sphere; and an implant. Computationally simulating the release of the pharmaceutical ingredient from the release system may comprise performing at least one direct numerical simulation of the physical properties governing the release by numerically solving partial differential equations governing the physical properties, the partial differential equations comprising at least one of: the Second Fick's law for diffusion; the Navier-Stokes equations for pressure gradient or flux driven flow; Ohm's law for electrical conductivity; and Fourier's law for thermal conductivity. Computationally simulating the release of the pharmaceutical ingredient from the release system may comprise performing at least one of: a finite volume numerical simulation, a finite difference numerical simulation, a finite element numerical simulation, and a Lattice Boltzmann numerical simulation.

In further related embodiments, the method may comprise employing voxels of the three-dimensional digital representation of the release system as a smallest computation cell in computationally simulating the release of the pharmaceutical ingredient from the release system. Each voxel of the voxels of the three-dimensional digital representation of the release system may comprise an integer value representing material phase information. The material phase information may comprise: at least one matrix phase; at least one pharmaceutical ingredient phase, and optionally at least one porosity phase. The method may comprise predicting the release rate of the pharmaceutical ingredient from the release system based on the three-dimensional digital representation of the release system, at least one physical property of the drug, and an established release model. The at least one physical property of the drug may comprise at least one of: an effective diffusivity coefficient, and a permeability. The established release model may comprise at least one of: a Higuchi thin plate model, a Higuchi cylinder model, and a Higuchi sphere model. The physical properties governing the release may comprise at least one of: a diffusion coefficient of a solute in a solvent, a concentration of the solute in the solvent, a mass flux of the pharmaceutical ingredient, a geometry of the sample of the release system, a loading of the pharmaceutical ingredient, a solubility of the pharmaceutical ingredient, a degradation profile of a solid non-drug material phase, and other relevant physical properties such as an electrical conductivity, a thermal conductivity, and a pressure gradient.

In another embodiment according to the invention, there is provided a computer system for predicting a release rate of a pharmaceutical ingredient from a release system. The computer system comprises a processor, and a memory with computer code instructions stored thereon. The processor and the memory, with the computer code instructions are configured to implement: a three-dimensional reconstruction module, the three-dimensional reconstruction module being configured to construct a three-dimensional digital representation of the release system based on physical imaging data of a sample of the release system, the three-dimensional digital representation satisfying a representative elementary volume evaluation of the pharmaceutical ingredient in the release system; and a release simulation module, the release simulation module being configured to computationally simulate the release of the pharmaceutical ingredient from the release system based on physical properties governing the release and on the three-dimensional digital representation of the release system. The release simulation module is further configured to base the computational simulation on at least one of: (i) a percolating network of porosity of the release system, and (ii) a percolating network of porosity formed as the pharmaceutical ingredient is released from the release system.

In further related embodiments, the three-dimensional reconstruction module may be configured to construct the three-dimensional digital representation by a process comprising, for at least one iteration: determining whether the three-dimensional digital representation of the release system satisfies the representative elementary volume evaluation; and, if the three-dimensional digital representation of the release system does not satisfy the representative elementary volume evaluation, revising the three-dimensional digital representation of the release system and again determining whether the three-dimensional digital representation of the release system satisfies the representative elementary volume evaluation. The three-dimensional reconstruction module may be configured to construct the three-dimensional digital representation by a process comprising, for at least one iteration: determining whether the three-dimensional digital representation of the release system satisfies the representative elementary volume evaluation; and, if the three-dimensional digital representation of the release system does not satisfy the representative elementary volume evaluation, using revised physical imaging data of a sample of the release system as the basis of the three-dimensional digital representation of the release system and again determining whether the three-dimensional digital representation of the release system satisfies the representative elementary volume evaluation. The physical imaging data of the sample of the release system may comprise three-dimensional imaging data. The physical imaging data of the sample of the release system may comprise two-dimensional imaging data. The three-dimensional reconstruction module may be configured to construct the three-dimensional digital representation of the release system based on at least one pre-existing three-dimensional digital representation of a release system with identical or similar design.

In other related embodiments, the three-dimensional reconstruction module may comprise an image segmentation module configured to perform image segmentation of physical imaging data to identify material phases in the physical imaging data. The image segmentation module may be configured to perform at least one of: an intensity-based image segmentation and a gradient-based image segmentation. The image segmentation module may comprise an artificial-intelligence based image segmentation module comprising human-trained image segmentation logic configured to recognize image features. The three-dimensional reconstruction module may be configured to construct the three-dimensional digital representation of the release system by a process comprising: processing the physical imaging data to produce pre-processed physical imaging data by performing at least one of: removal or reduction of imaging artifacts, calibration of imaging contrast, and enhancement of image features; performing image segmentation of the pre-processed physical imaging data to identify material phases in the physical imaging data, thereby producing segmented image data; and performing microstructure post-processing of the segmented image data.

In further related embodiments, the release simulation module may be configured to computationally simulate the release of the pharmaceutical ingredient from the release system by at least one of: performing an empirical-based release simulation; performing a reduced order geometry-based release simulation; performing a geometry-based release simulation; and performing a voxel-based release simulation. The release simulation module may further comprise a non-dimensional release profile module configured to perform a percolation-based simulation to determine a non-dimensional release profile comprising an amount of pharmaceutical ingredient released at each simulated non-dimensional step of a layer by layer release of the pharmaceutical ingredient proceeding from an exterior surface of the release system to an interior surface of the release system. The release simulation module may further comprise an intermediate release stage module configured to perform a percolation-based simulation to determine an intermediate release stage microstructure for each simulated non-dimensional step of a layer by layer release of the pharmaceutical ingredient from the release system, the layer by layer release proceeding from an exterior surface of the release system to an interior surface of the release system. The release simulation module may further comprise an effective diffusivity coefficient module configured to use the determined intermediate release stage microstructures to determine an effective diffusivity coefficient. The release simulation module may be further configured to: determine concentration distribution of the pharmaceutical ingredient throughout the percolating network of porosity based on solving flux balance with a finite volume method; and based on the concentration distribution, determining the effective diffusivity coefficient. The release simulation module may be further configured to determine the effective diffusivity coefficient based on direct numerical simulation employing voxels of the three-dimensional digital representation of the release system as a smallest computation cell of the direct numerical simulation. The release simulation module may be further configured to predict the release rate of the pharmaceutical ingredient from the release system based on at least: (i) the non-dimensional release profile and (ii) the effective diffusivity coefficient.

In other related embodiments, the release simulation module may be further configured to: perform a first simulation based on physical imaging data obtained at a first resolution scale; and perform a second simulation based on physical imaging data obtained at a second resolution scale, different from the first resolution scale. The first simulation may comprise a percolation-based simulation based on physical imaging data obtained at the first resolution scale; and the second simulation may comprise an effective diffusivity simulation based on physical imaging data obtained at the second resolution scale. The physical imaging data may comprise images produced from at least one of: computed tomography; focused ion beam scanning electron microscopy; magnetic resonance imaging; ultrasound imaging; light microscopy; transmission electron microscopy; Raman Imaging; and atomic force microscopy. The release system may comprise at least one of: a drug; a medical device; and biological tissue. The drug may comprise at least one of: a tablet; a pellet; a spray-dried particle; a lyophilized solid; a micro-sphere; a nano-sphere; and an implant. The release simulation module may be configured to computationally simulate the release of the pharmaceutical ingredient from the release system by a process comprising performing at least one direct numerical simulation of the physical properties governing the release by numerically solving partial differential equations governing the physical properties, the partial differential equations comprising at least one of: the Second Fick's law for diffusion; the Navier-Stokes equations for pressure gradient or flux driven flow; Ohm's law for electrical conductivity; and Fourier's law for thermal conductivity. The release simulation module may be configured to computationally simulate the release of the pharmaceutical ingredient from the release system by performing at least one of: a finite volume numerical simulation, a finite difference numerical simulation, a finite element numerical simulation, and a Lattice Boltzmann numerical simulation.

In further related embodiments, the release simulation module may be configured to employ voxels of the three-dimensional digital representation of the release system as a smallest computation cell in computationally simulating the release of the pharmaceutical ingredient from the release system. Each voxel of the voxels of the three-dimensional digital representation of the release system may comprise an integer value representing material phase information. The material phase information may comprise: a matrix phase; at least one pharmaceutical ingredient phase, and optionally at least one porosity phase. The release simulation module may be configured to predict the release rate of the pharmaceutical ingredient from the release system based on the three-dimensional digital representation of the release system, at least one physical property of the drug, and an established release model. The at least one physical property of the drug may comprise at least one of: an effective diffusivity coefficient, and a permeability. The established release model may comprise at least one of: a Higuchi thin plate model, a Higuchi cylinder model, and a Higuchi sphere model. The physical properties governing the release may comprise at least one of: a diffusion coefficient of a solute in a solvent, a concentration of the solute in the solvent, a mass flux of the pharmaceutical ingredient, a geometry of the sample of the release system, a loading of the pharmaceutical ingredient, a solubility of the pharmaceutical ingredient, a degradation profile of a solid non-drug material phase, and other relevant physical properties such as an electrical conductivity, a thermal conductivity, and a pressure gradient.

In other related embodiments, the computer system may further comprise one or more storage units; the memory may comprise at least one memory unit; and the processor may comprise at least one processor unit. The computer system may further comprise a user interface that is configured to permit a user to at least one of access, manage and visualize at least one of: imaging data, derived data, image processing tasks, simulation tasks and hardware resources. The user interface may comprise a graphical user interface. The user interface may be at least one of desktop-based or cloud-based.

In another embodiment according to the invention, there is provided a non-transitory computer-readable medium configured to store instructions for predicting a release rate of a pharmaceutical ingredient from a release system, the instructions, when loaded and executed by a processor, cause the processor to predict the release rate of the pharmaceutical ingredient from the release system by: constructing a three-dimensional digital representation of the release system based on physical imaging data of a sample of the release system, the three-dimensional digital representation satisfying a representative elementary volume evaluation of the pharmaceutical ingredient in the release system; and computationally simulating the release of the pharmaceutical ingredient from the release system based on physical properties governing the release and on the three-dimensional digital representation of the release system, the computational simulation being further based on at least one of: (i) a percolating network of porosity of the release system, and (ii) a percolating network of porosity formed as the pharmaceutical ingredient is released from the release system.

BRIEF DESCRIPTION OF THE DRAWINGS

The foregoing will be apparent from the following, more particular, descriptions of example embodiments, as illustrated in the accompanying drawings in which like reference characters refer to the same parts throughout the different visuals. The drawings are not necessarily drawn to scale in order to emphasize the embodiments.

FIG. 1A is a two-dimensional scanning electron microscope image of a drug with a porous matrix dispersed with the API. FIG. 1B is a three-dimensional digital representation of the same drug as in FIG. 1A. FIG. 1C is a two-dimensional scanning electron microscope image of a drug with a solid non-porous matrix dispersed with the API, where the API internal to the drug will release through the porous media created by the release of the API external to the drug.

FIG. 1D is a three-dimensional digital representation of the same drug as in FIG. 1C.

DETAILED DESCRIPTION

A description of example embodiments follows.

Figure 1A:
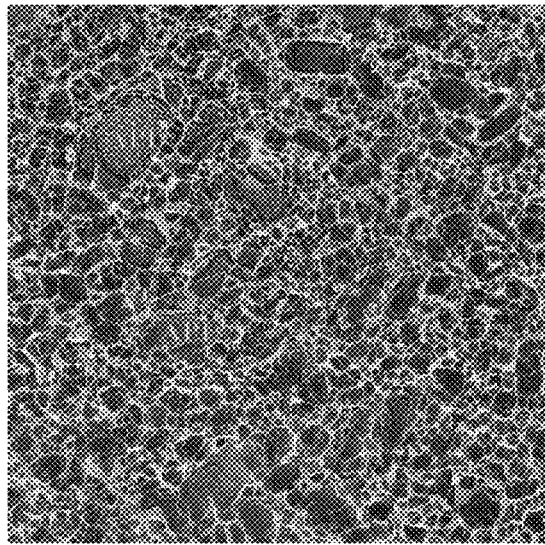
FIG. 1A-1D are example images of extended release drug designs in accordance with the prior art.
Figure 1B:
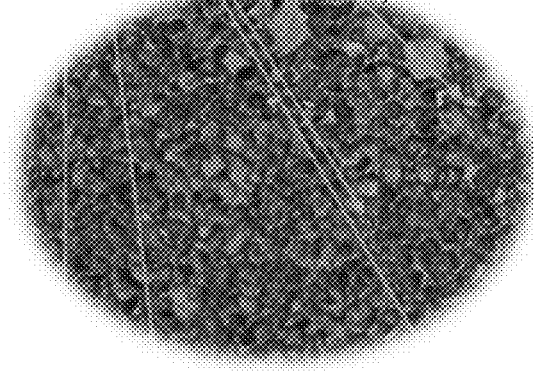
Figure 1C:
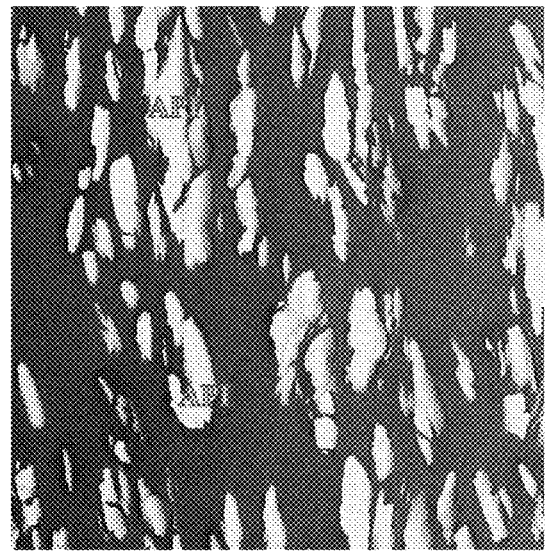
Figure 1D:
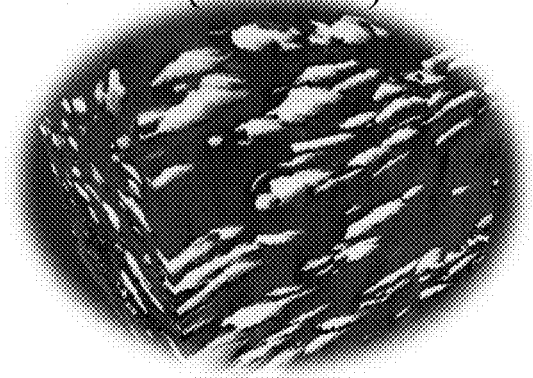

An embodiment according to the invention relates in part to a method for computing the release rate for a drug or medical device. One embodiment is used for a long-acting parenteral (LAP) controlled release drug. Due to the often utilized extended release (ER) design, LAP can maintain therapeutic drug concentration over extended durations, thus reducing dosing frequency, improving patient adherence and enhancing treatment outcome [Brissons et. al., Ther. Adv. Psychopharmacology, 4(5) 2014 198-219] [Grimaldi-Bensouda, et. al., Schizophrenia Research, 134 (2012) 187-194]. Various LAP delivery systems are successfully applied in the prevention and treatment of infectious diseases, such as HIV/AIDS [Landovitz, Curr. Opin. HIV AIDS, 11(1) 2016 122-128]. FIG. 1 shows two examples of ER designs. On the left, FIG. 1A is a scanning electron microscope (SEM) image. Drug particles are embedded in a porous polymer excipient. Body fluid has to infiltrate the porous polymer excipient before it can progressively come in contact with the API. FIG. 1B is a three-dimensional digital representation of the drug particle distribution inside the porous polymer excipient matrix. FIG. 1C, by comparison, illustrates the SEM image of a different ER design. In this case, drug particles are embedded in a non-porous polymer matrix. However, the drug particles are dispersed into the polymer in a way that allows them to be interconnected. Patient's body fluid first dissolves the drug that is at the exterior surface of the sample. The released drug will form a pore space. The continuous release from the exterior surface to the interior of the drug will form a percolating porous network, through which the remaining drug inside the sample will find its way out. FIG. 1D shows a three-dimensional digital representation of the drug particle distribution.

The LAP design requires a very long time to complete a laboratory release test, so there is a need for an alternative, more efficient method. In addition to the time concern, LAP dosage forms are inherently complex and consist of a wide range of delivery platforms including: micro- and nanoparticulate systems, in-situ forming gels, and pre-formed implants for subdermal insertion. Delivery platforms often use a polymer as a rate-limiting matrix or membrane to achieve extended drug release, due to its unique physical properties, robustness and processability. The ER rate of these formulations is influenced by the physiochemical properties of the drug itself, the polymer, and the potential interaction between the drug and the polymer [Siepmann et. al., 2012]. The interplay of formulation, material properties, manufacturing process and release environment complicates a LAP controlled release design. Characterization using conventional laboratory based methods are very challenging due to insufficient resolutions and lengthy time. Therefore, novel characterization tools and analysis approaches, such as a high resolution imaging technique, advanced imaging analytics and image-based modelling and simulation, can be very beneficial for fundamentally understanding and predicting extended drug release performance. These novel characterization tools and analysis approaches can predict release profile accurately and efficiently, and ultimately aid in the design of robust, efficacious and scalable implant formulations.

Figure 2:
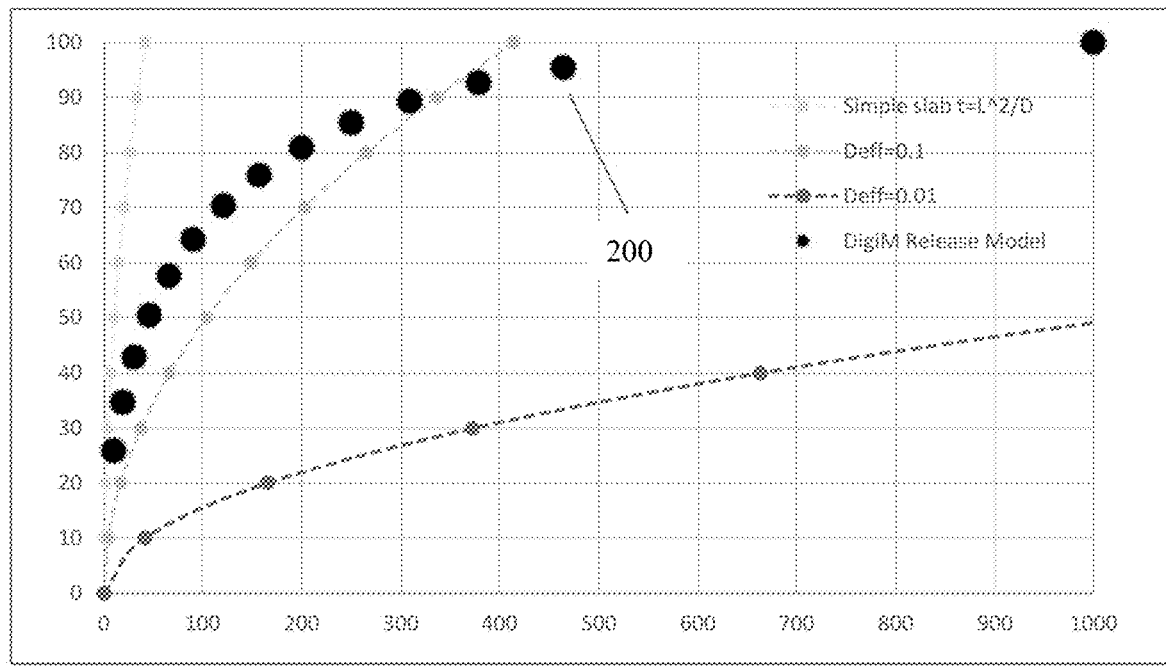
FIG. 2 is a graph showing examples of release profiles, including a release profile 200 of a controlled release drug determined in accordance with an embodiment of the invention.

FIG. 2 shows a typical release profile corresponding to the controlled release drug design of FIG. 1C in accordance with an embodiment of the invention.

An image-based release rate method in accordance with an embodiment of the invention combines an experimental approach (imaging) with the numerical modeling approach. There are a few advantages over a conventional experimental approach, as follows.

a. An image-based release rate computation method is one or two orders of magnitude faster than a physical release test. The test cycle timeline can be reduced from weeks (controlled release design) or months (extended release design) to days. Due to reduced time, more parameters can be covered.

b. Image-based computation method can obtain multiple physical properties on the drug same sample, such as a diffusivity coefficient for diffusion-driven release, permeability for osmic pressure-driven release, and Young's modulus for polymer-drug interaction. When compared to a physical experiment, image-based computation method allows for a simpler way to correlate measurements of different physical properties obtained from separate specimens.

c. Image-based computation method allows for modifications of drug microstructures in a cost effective manner, instead of manufacturing of new samples.

d. In image-based release rate computation method, fluid conditions can be modified to mimic any in-vitro or in-vivo release environment.

Like any new method, careful validation is important for image-based release rate computation method.

Overall Workflow

Figure 3:
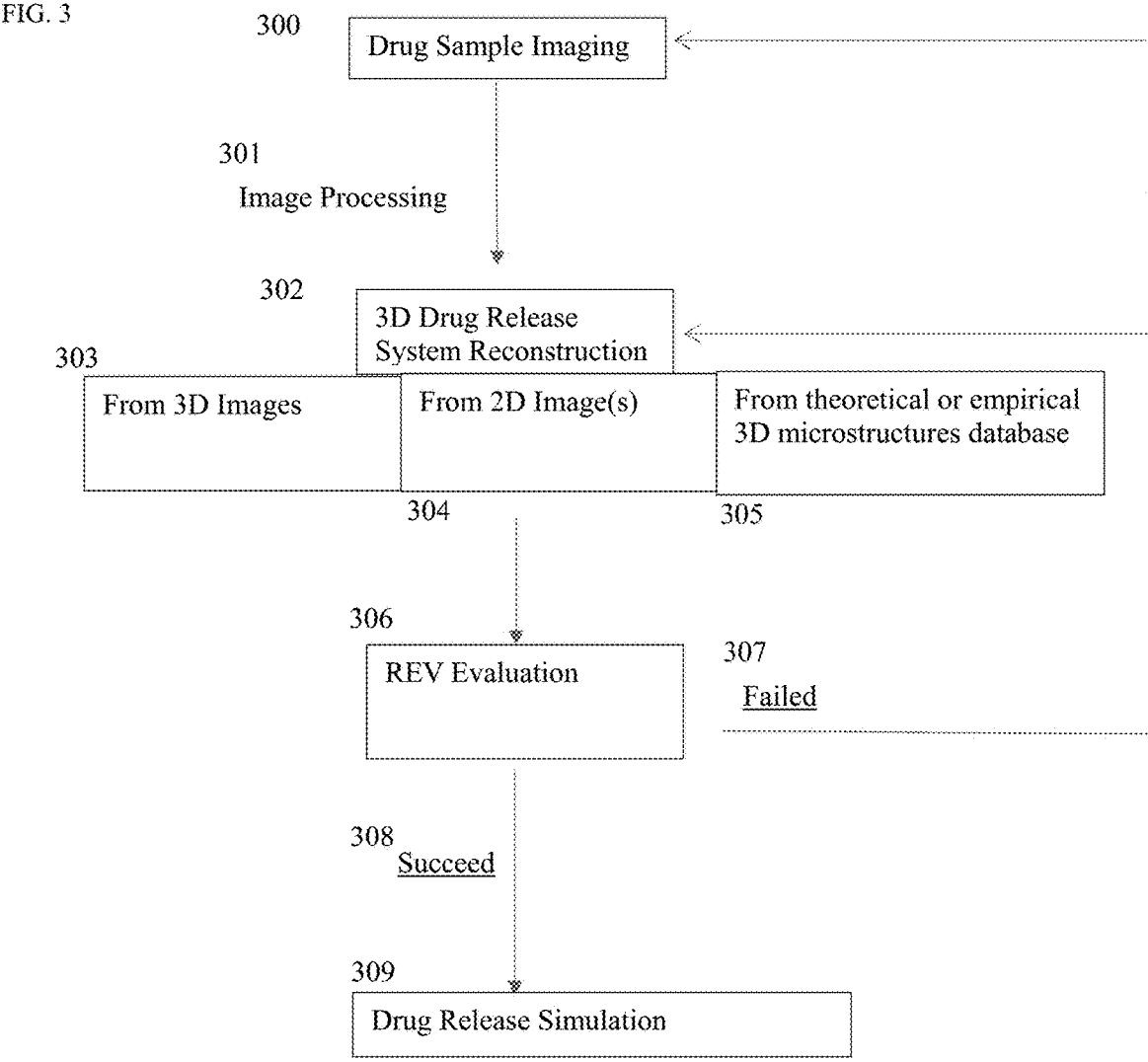
FIG. 3 is a schematic block diagram of a computer-implemented method of predicting the release rate of a pharmaceutical ingredient from a release system in accordance with an embodiment of the invention.

An image-based drug release computation method, in accordance with an embodiment of the invention, has four primary steps 300, 302, 306 and 309, as illustrated in the workflow diagram in FIG. 3. It starts with imaging experiments (300) at the appropriate resolution using the appropriate imaging device. In a controlled release drug characterization embodiment, focused ion beam scanning electron microscopy (FIB-SEM) can be used to collect hundreds of images from the sample.

After an appropriate image processing and segmentation of the images (301), a three-dimensional volumetric digital representation (302) of the drug release system will be reconstructed. In one embodiment, the three-dimensional digital representation is reconstructed from three-dimensional images (303). In other cases, it can be reconstructed from a two-dimensional image (304), or from theoretically or empirically existing three-dimensional digital representations (305) constrained by the imaging data of current drug sample. The three-dimensional digital representation is composed of voxels, which are three-dimensional correspondence of image pixels. Each voxel contains material phase information represented by an integer value. For example, in the controlled release formulation shown in FIG. 1C, three material phases are represented as 0—polymer matrix, 1—porosity (after drug is released), and 2—drug.

In accordance with an embodiment of the invention, the three-dimensional digital representation is assessed against a representative elementary volume (REV) criterion (306). In the theory of composite materials, the representative elementary volume (REV), also referred to as the representative volume element (RVE) or the unit cell, is the smallest volume over which a measurement can be made that will yield a value representative of the whole sample. [Hill, R. (1963), "Elastic properties of reinforced solids: some theoretical principles." *Journal of the Mechanics and Physics of Solids,* 11 (5): 357-372]. In the case of periodic materials, one simply chooses a periodic unit cell (which, however, may be non-unique), but in random media, the situation is much more complicated. For volumes smaller than the REV, a representative property cannot be defined and the continuum description of the material involves the Statistical Representative Elementary Volume (SREV) and random fields. The property of interest can include mechanical properties such as elastic moduli, transport properties, electromagnetic properties, thermal properties, and other averaged quantities that are used to describe physical systems. For an embodiment of the invention, drug volume fraction is used as a REV criterion. For example, assume the three-dimensional digital representation has 1000×1000×1000 voxels at 0.1 um resolution. Thus, it digitizes a drug sample volume of 100×100×100 μm³. The smallest feature, i.e., the smallest possible drug particle and its connection to its neighbor particle (called neck) is 0.1 μm in theory. In practice, however, the smallest feature that can be resolved is 2-5 times of the resolution, or 0.2-0.5 μm, depending on the signal to noise ratio of the particular imaging experiment. Volume fraction REV evaluation starts with a small volume, e.g., 100×100×100 voxels, and progressively increases the volume, e.g., by 100 voxels in all three dimensions per step. At each intermediate step, the volume fraction is assessed on a sub-volume of 200×200×200, or 300×300×300, and so on. If the volume fraction reaches a substantially constant value, a REV is obtained. Further steps can be carried out with either the full volume, or a subset at which REV has been achieved.

As used herein, a three-dimensional digital representation is considered to satisfy a representative elementary volume evaluation of the pharmaceutical ingredient in the release system when the volume fraction of the pharmaceutical ingredient reaches a substantially constant value as compared to successively increasing sample volumes; where a "substantially constant value" is the difference from a preceding volume fraction that is desired and appropriate for a given application of predicting the release rate for a given release system, over one or more, or an appropriate number of, successive increases of sample volumes. For example, without limitation, a substantially constant value may be reached when the volume fraction of the pharmaceutical ingredient comprises less than about a 10% difference from a preceding volume fraction, less than about a 5% difference from a preceding volume fraction, less than about a 2% difference, less than about a 1% difference, less than about a 0.1% difference, less than about a 0.01% difference, or less than about a 0.001% difference. In addition, it will be appreciated that other approaches to determining a representative elementary volume (REV) and Statistical Representative Elementary Volume (SREV) can also be used, and are consistent with the teachings herein.

In accordance with an embodiment of the invention, if the REV criterion fails (307), a first step in reconstruction can be to regenerate the three-dimensional digital representation with additional constraints; and then, if that does not work, the physical imaging can be re-conducted, regenerating the three-dimensional digital representation and evaluating it relative to the REV criterion. In one example of regeneration, a three-dimensional representation, or a portion thereof, can be revised by mirroring the representation, or a portion of it, and again performing the REV evaluation on the resulting three-dimensional representation. Alternative or additional regeneration steps can be used and are consistent with the teachings herein.

After the REV criterion has been met (308), release simulation (309) is then conducted on the three-dimensional volumetric digital representation of the drug release system to predict the drug release profile, such as FIG. 2. In accordance with an embodiment of the invention, the drug release simulation can, for example, be empirical-based, reduced order geometry-based, geometry-based or voxel-based.

Imaging of Drug Sample

For the FIB-SEM imaging experiment performed in accordance with an embodiment of the invention, a Zeiss Auriga crossbeam system with a Ga+ ion beam gun is used. This sample, like many pharmaceutical samples, is non-conductive. A conductive coating layer is deposited to avoid electron charging that may lead to imaging experiment failure. One front and two side trenches are made around the region of interest to get it exposed to the FIB slicing process and to minimize the possibility of material re-deposition during slicing. For each FIB slicing step, a layer (e.g., 30 nm thick) of material is removed and one or multiple high resolution SEM images are collected with a back-scattered electron (BSE) detector, secondary electron (SE) signals, or a combination of different detectors. Hundreds of images (e.g., six hundred) are collected via iterative FIB slicing and SEM imaging.

While FIB-SEM is one method to acquire three-dimensional images, other three-dimensional imaging methods can be used to digitize the sample, including CT, MicroCT, UAI, LM, TEM, RI, AFM, and others, as far as the imaging experiment can capture the structures of the drug release systems with appropriate contrast and resolution.

In some cases, three-dimensional imaging is either impossible (e.g., RI and AFM), or undesirable due to cost or time concerns. One or multiple two-dimensional images can be taken instead, and later used to reconstruct a three-dimensional micro-structure (304). Images can also be used as guidance and constraints to a match during a search in theoretical or empirical micro-structure database.

In some other cases, a correlative imaging approach is needed for both high enough resolution and representative enough field of view. For example, MicroCT and FIB-SEM are two commonly used correlative imaging platforms.

Three-Dimensional Digital Representation of the Drug Release System

Figure 4:
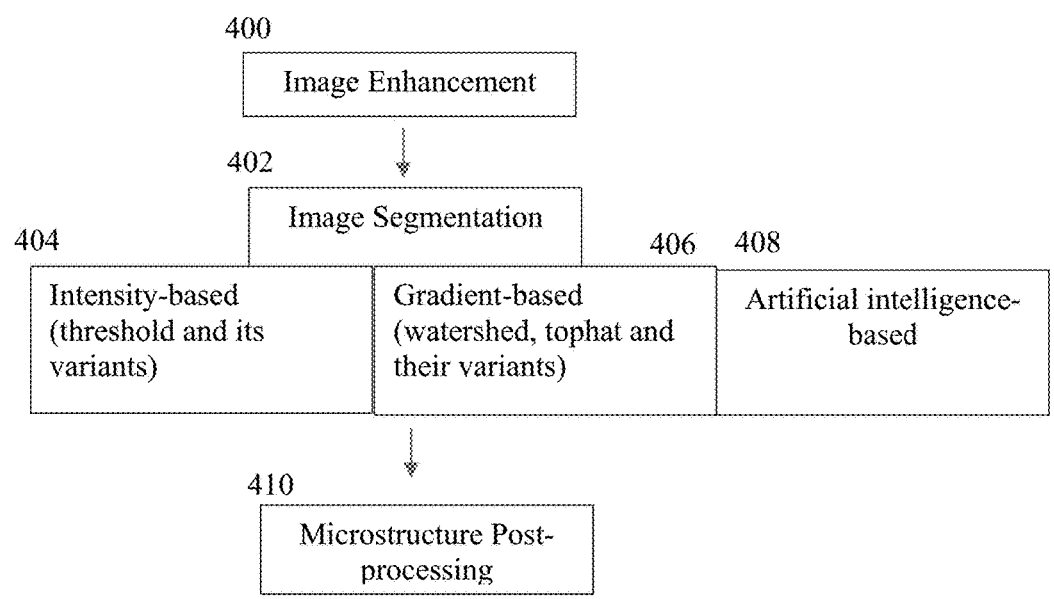
FIG. 4 is a schematic block diagram of a computer-implemented method of image-based reconstruction of a three-dimensional digital representation of a drug release system in accordance with an embodiment of the invention.

In accordance with an embodiment of the invention, based on a processed image data (301), a three-dimensional digital representation of the drug release system (302) will be reconstructed. Three steps can be involved in image processing, as shown in FIG. 4. First, image quality is improved (400) so that the imaging artifact is removed or reduced; imaging contrast is calibrated; and features are enhanced through noise reduction. Then image segmentation (402) is performed to identify material phases. In accordance with an embodiment of the invention, segmentation is done using for examples an intensity-based algorithm (404), such as threshold and its variants where material phases are assigned to regions of an image based on whether the intensity exceeds or does not exceed a given grayscale threshold intensity value; or a gradient-based algorithm (406), such as watershed, tophat and their variants; an artificial intelligence-based algorithm (408); or others. As a third step, post-processing (410) on the microstructures segmented may be necessary in order to maintain quality control over the digital representation. From segmented images, a three-dimensional digital representation of the drug release system is either reconstructed from a three-dimensional image segmentation, reconstructed from one or multiple two-dimensional image segmentations, or generated from theoretical or empirical models of previous three-dimensional digital representations (for example, from a three-dimensional digital representation database) using the imaging data from current sample as a constraint.

Figure 12:
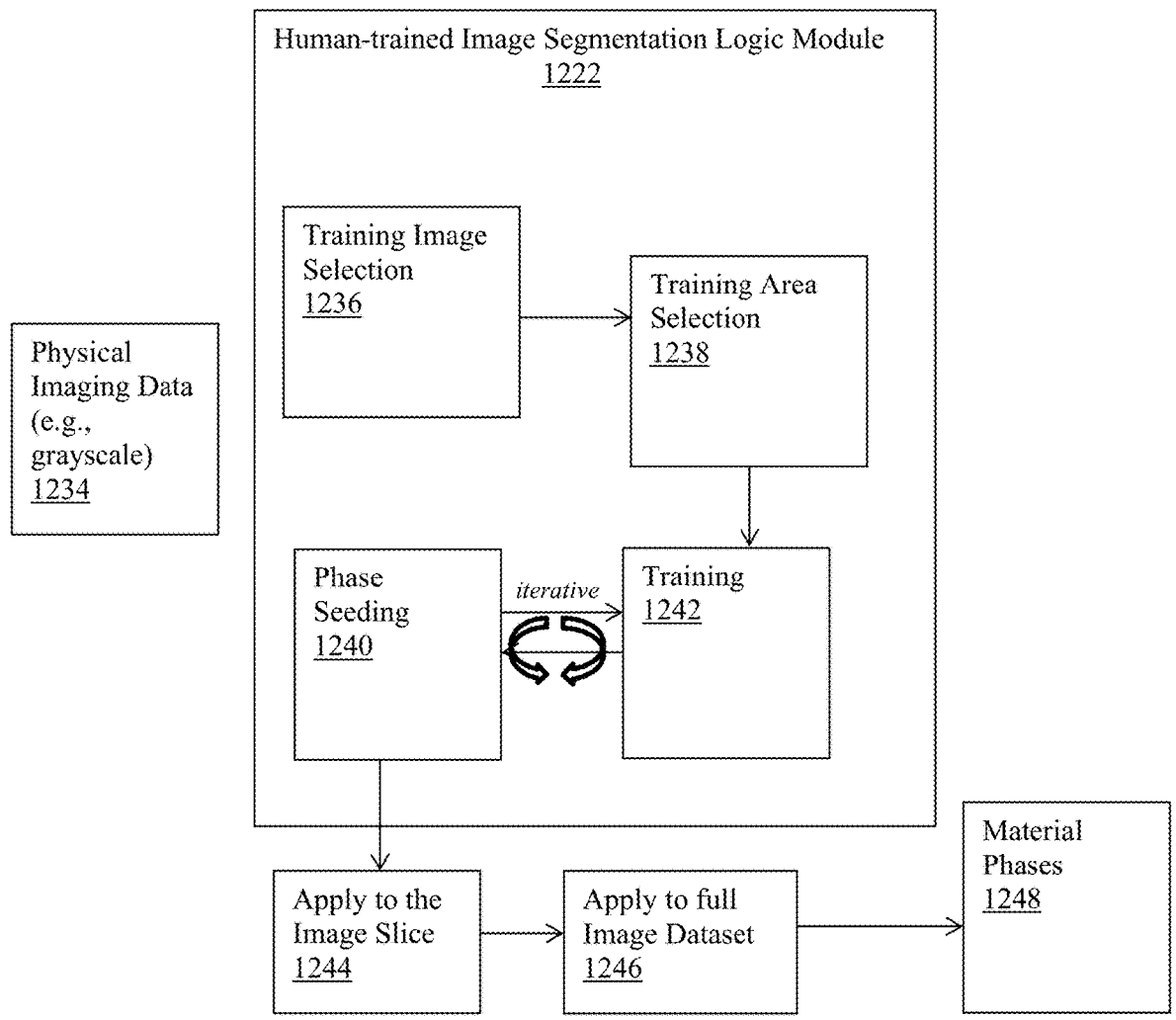
FIG. 12 is a schematic block diagram of a human-trained image segmentation logic module in accordance with an embodiment of the invention.

In accordance with an embodiment of the invention, in order to translate the massive amount of imaging data into three-dimensional digital representation that can be quantified and used to perform numerical simulations on drug release performance, appropriate image segmentation is essential. Otherwise, inaccurate segmentation can render anything computed afterwards useless. Furthermore, it is necessary to automatically process many images within a reasonable amount of time. To perform image segmentation with both accuracy and efficiency, an artificial intelligence-based image segmentation (AIBIS) algorithm is used in accordance with an embodiment of the invention. AIBIS learns from human vision intelligence, which recognizes a feature not only via the grayscale value of pixels, but also from its relationships with the surrounding pixels. The collection of the pixels reflects a unique signature of a material phase in response to the imaging signal as a textural pattern. AIBIS is first trained by a human operator to recognize all the features on a small seed image. Once the training on the seed image is considered satisfactory, the trained image segmentation logic can be populated not only to all the images in the current sample, but also to the images collected under a calibrated imaging condition on different samples with similar material phases. [S. Zhang. DigiM Artificial Intelligence Image Processing. DigiM Technology Highlight 2017 July Issue. Jul. 29, 2017.] In accordance with an embodiment of the invention, image segmentation can be performed using artificial intelligence-based image segmentation, such as, for example, using a human-trained image segmentation logic module to recognize image features, as described below in connection with FIG. 12.

Once the images are segmented into multiple phases (drug, polymer, air, etc.), a numerical analysis is conducted on each phase in order to obtain a quantitative database of microstructures of the drug/polymer implant formulation for simulating release performance.

Image-Based Drug Release Prediction

In accordance with an embodiment of the invention, the three-dimensional digital representation of the drug release system is used to predict drug release performance.

In one embodiment, drug particles are dispersed into the polymer excipient matrix while maintaining an interconnected network. When the drug is in contact with the release environment, e.g., body fluid, the API particles at the surface of the drug will first be in contact with the liquid in the release environment. The API will dissolve into the liquid and leave the drug sample. This initial release is constrained by the dissolution limit of the API compound. In the drug sample, the space vacated by the API will be filled with liquid, creating a porous polymer media between the remaining API (further inside the drug) and the release environment (outside the drug). The remaining API inside the drug sample will release through the porous polymer layer. The thickness of this porous polymer layer will increase in time, which leads to increasing tortuosity, decreasing effective diffusivity, and decreasing release rate.

Figure 5:
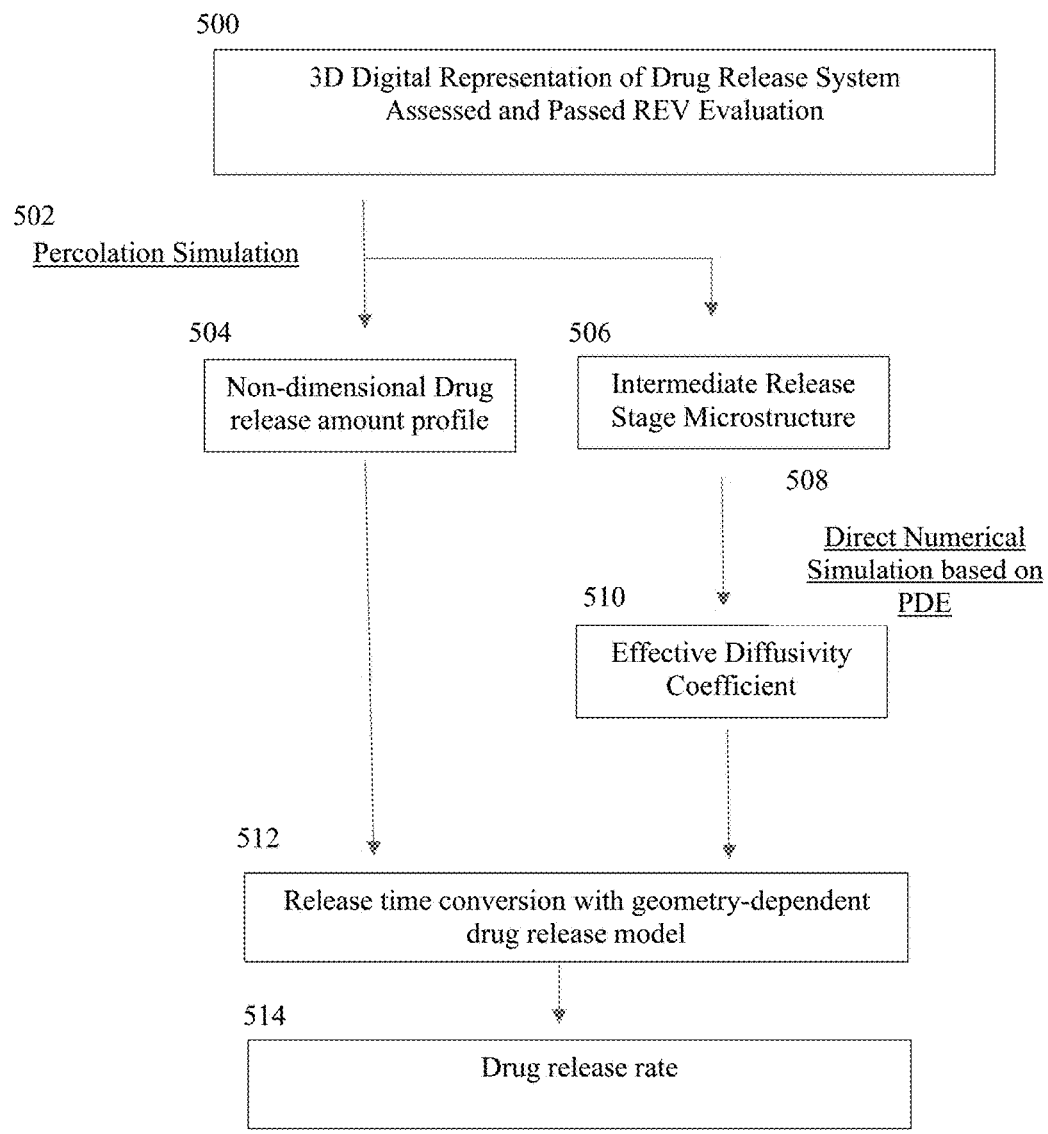
FIG. 5 is a schematic block diagram of a computer-implemented method of image-based release prediction in accordance with an embodiment of the invention.

In an embodiment according to the invention, the drug release simulation has three components as shown in the flow diagram of FIG. 5: percolation simulation (502), direct numerical simulation for effective diffusivity coefficient (508) and release time conversion with geometry-dependent drug release model (512).

Starting with a three-dimensional digital representation of a drug release system satisfies REV evaluation (500), the first component of the drug release simulation is a voxel-based percolation-simulation (502) to determine the amount of drug released at each step. In this simulation step, interconnected drug particles are released layer by layer from an exterior surface to an interior location of the drug. The smallest amount of drug released from each layer is dictated by the resolution of the three-dimensional digital representation of the drug release system. This simulation produces a non-dimensional drug release profile (504) with an x axis representing the steps (non-dimensional) and a y axis representing the amount of drug released $$\frac{V_{i-1}}{V_\infty}.$$

Figure 6:
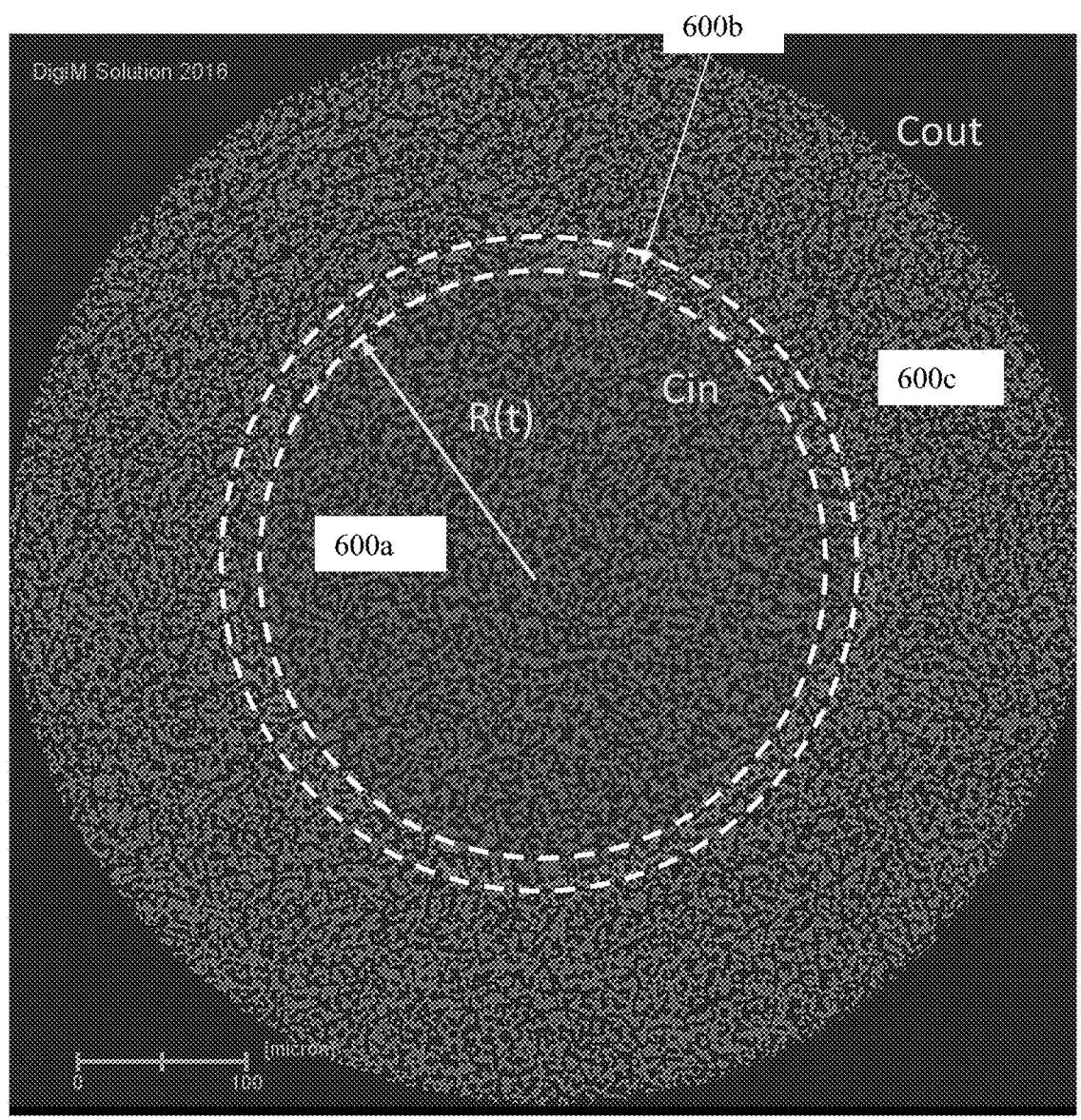
FIG. 6 is a diagram of intermediate microstructures of the digital drug release system determined in accordance with an embodiment of the invention.

In the meanwhile, intermediate release stage microstructures (506) will be determined for each release step, as shown in FIG. 6. Each of these intermediate release stage microstructures include the amount of the drug remaining (material phase 600a in FIG. 6); the amount of drug released, hence the original space it occupied before becoming porous (material phase 600c in FIG. 6); and the infinitesimal drug layer currently being released (material phase 600b in FIG. 6, exaggerated from the actual one voxel thickness).

In the second component of FIG. 5, the porous media (material phase 600c in FIG. 6) from the intermediate release stage is used as the input of direct numerical simulation for effective diffusivity based on partial differential equations (PDE) (508). Second Fick's law is used to solve flux balance with finite volume method through interconnected voxels of the porous media, $$\frac{\partial C}{\partial t} = D_{bulk} \nabla^2 C$$

Where
$D_{bulk}$: diffusion coefficient of the solute in the solvent
C: concentration of the API in the solvent
Dirichlet boundary conditions is used, where,
Cin=1.0
Cout=0.0
This simulation produces concentration distribution throughout the porous media (material phase 600c in FIG. 6). Then using the resulting concentration, an effective diffusivity coefficient (510) can be derived according to Fick's first law rearranged, $$D_{eff} = \frac{\vec{j}}{\vec{\nabla} C}$$

Where
$\vec{j}$ is mass flux of the drug API
$\vec{\nabla} C$ is the API concentration gradient between Cin and Cout In accordance with an embodiment of the invention, a voxel-based direct numerical simulation method is used for an optimal balance of accuracy and computation efficiency. Voxels from the three-dimensional digital representation are used as the smallest computation cell. Other alternative approaches that can be used include empirical models (such as averaging pore size from the voxels and correlating it with tortuosity and diffusivity coefficient), reduced order geometry model (such as simplifying connected voxels of a material phase into a pore network model with balls and sticks), Lattice Boltzmann method or other meshless methods, or finite element method, finite volume method, finite difference method or reduced-order model method on conventional smooth surface mesh, and are consistent with the teachings herein.

The third component 512 in FIG. 5 converts numerical, non-dimensional release steps into physical time. In accordance with an embodiment of the invention, it is a function of geometry of the drug sample, drug loading, drug solubility, and effective diffusivity coefficient. In accordance with an embodiment of the invention, when the drug geometry is a cylinder or similar, the following Higuchi release model is used:

$$t = \left[\frac{V_i}{V_\infty} + \left(1 - \frac{V_i}{V_\infty}\right)\ln\left(1 - \frac{V_i}{V_\infty}\right)\right] \cdot \frac{R^2}{4 \cdot \frac{C_s}{C_0} \cdot D_{eff}}$$

Where
$\frac{V_i}{V_\infty}$ is the same as $\frac{M_i}{M_\infty}$

R is the radius of the sample
Cs is drug substance concentration at drug solution interface, which is typically determined with drug substance solubility test.
C0 is initial bulk drug concentration, which is derived from drug loading.
The time required for each infinitesimal drug layer to release through the progressively thicker porous layer is computed. Other models can be used including, but not limited to, Higuchi models and variations for monolithic release, membrane models, and others [Siepmann et. al., 2012].

The result of the embodiment of FIG. 5 is the drug release rate, 514.

Variations on the Application of an Embodiment of the Invention for Drug Release Systems with Strong Heterogeneity In case of a well dispersed, relatively homogeneous system, one image data with single resolution is sufficient for release prediction. For example, when the drug particle sizes are relatively uniform with size ranges less than one order of magnitude in scale, single resolution is sufficient to resolve both the particles and their contacts (neck). However, when the drug particles are not well dispersed, their neck becomes smaller, which requires higher resolution to resolve. When such high resolution is engaged, the sample size that can be imaged reduces. The representativeness of the interconnected drug particle network is lost. Consequently, a multi-scale, correlative imaging approach is necessary to capture both the particle network and the neck. In accordance with one embodiment of the invention, the lower resolution data captures the particle network that is representative to the sample, while the high resolution data captures the smallest necks and physical properties they control. For example, in accordance with one embodiment of this invention, a controlled release design similar to the embodiment discussed above, but has API particle sizes of a few microns to a few 10s of microns. It requires MicroCT data imaged at 0.5-2 µm resolution to capture a representative network of the interconnected drug phase (Percolation simulation 502). FIB-SEM data imaged at 5-10 nm resolution is used for effective diffusivity simulation (508) in which the smallest neck of adjacent particles is considered. The FIB-SEM-based results will be integrated to MicroCT data in step 510.

In accordance with one embodiment of this invention, variations on systems that require more than two scales of imaging can be iteratively constructed.

Systems and Software

Figure 7:
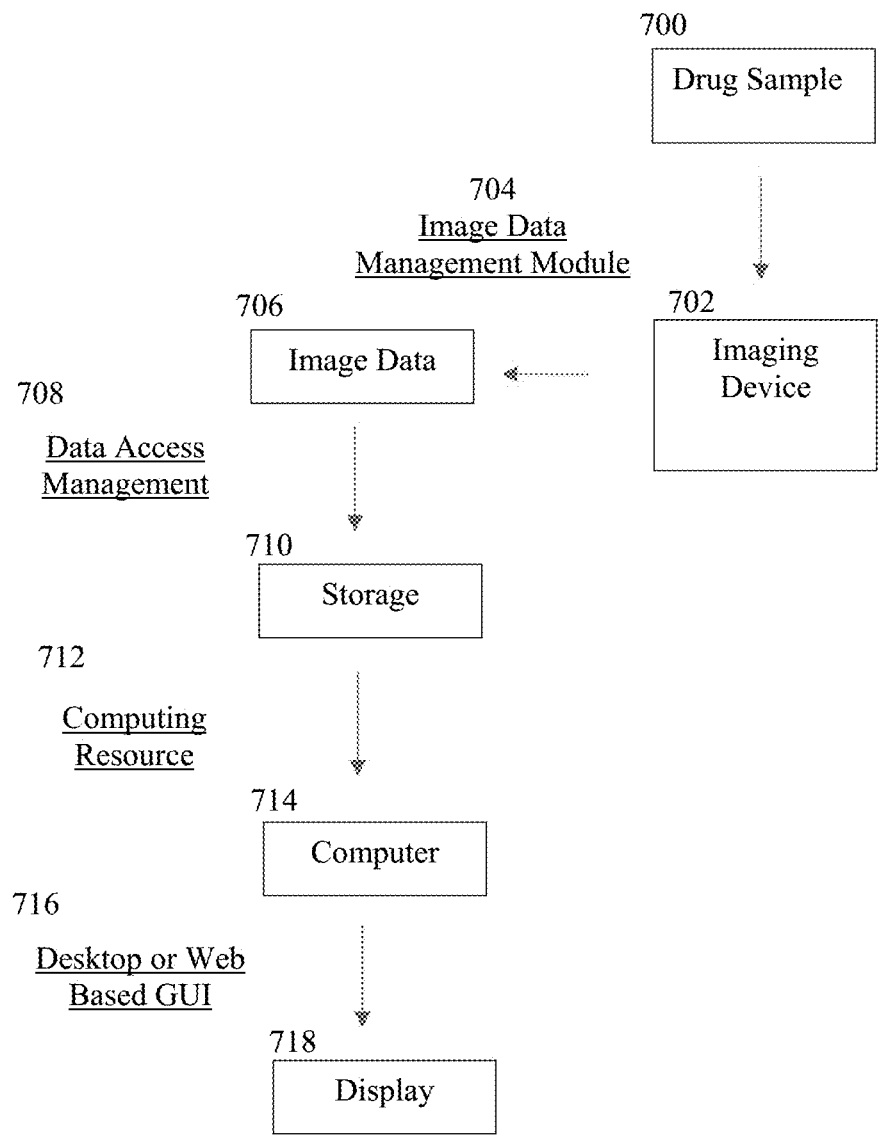
FIG. 7 is a schematic block diagram of a system for predicting a release rate of a pharmaceutical ingredient from a release system in accordance with an embodiment of the invention.

An embodiment according to the invention also relates to a system for computing release rate for the drug or medical device, starting from a drug sample (700), as shown in FIG. 7.

(a). An imaging device (702) that is capable of producing image data (706) at a desirable resolution and contrast for the specific drug or medical device sample, that can be stored on a storage device (710), through image data management (704) and data access management (708) modules.

(b). One or multiple computers (714) operable for executing computer programs that, through necessary computing resource management modules (712), can:

reconstruct a three-dimensional digital representation of the drug release system simulate drug release and correlate the drug release amount with physical time manage storage and access to imaging data, derived data, and computer programs for previous computing tasks (c). A graphical user interface that allows the user to operate on the aforementioned computer(s), programs, and storage, which can be desktop based or cloud based (716).

(d) A display (718) that can be a computer monitor, television, video camera, mobile device, or others.

Figure 8:
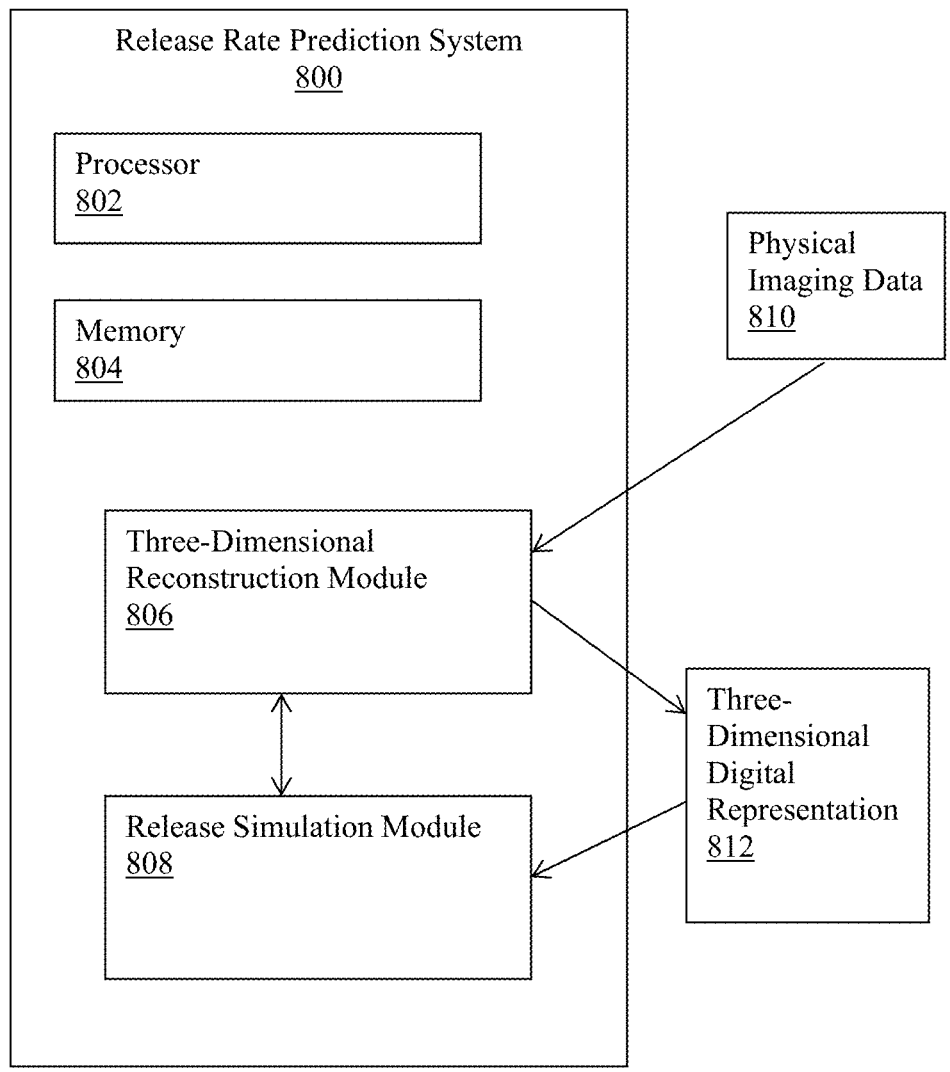
FIG. 8 is a schematic block diagram of a release rate prediction system in accordance with an embodiment of the invention.

FIG. 8 is a schematic block diagram of a release rate prediction system 800, in accordance with an embodiment of the invention. The computer system 800 predicts a release rate of a pharmaceutical ingredient from a release system, and comprises a processor 802, and a memory 804 with computer code instructions stored thereon. The processor 802 and the memory 804, with the computer code instructions, are configured to implement a three-dimensional reconstruction module 806 and a release simulation module 808. The three-dimensional reconstruction module 806 is configured to construct a three-dimensional digital representation 812 of the release system based on the physical imaging data 810 of a sample of the release system. The three-dimensional digital representation satisfies a representative elementary volume evaluation of the pharmaceutical ingredient in the release system. The release simulation module 808 is configured to computationally simulate the release of the pharmaceutical ingredient from the release system based on physical properties governing the release and on the three-dimensional digital representation of the release system. The release simulation module 808 is further configured to base the computational simulation on at least one of: (i) a percolating network of porosity of the release system, and (ii) a percolating network of porosity formed as the pharmaceutical ingredient is released from the release system.

Figure 9:
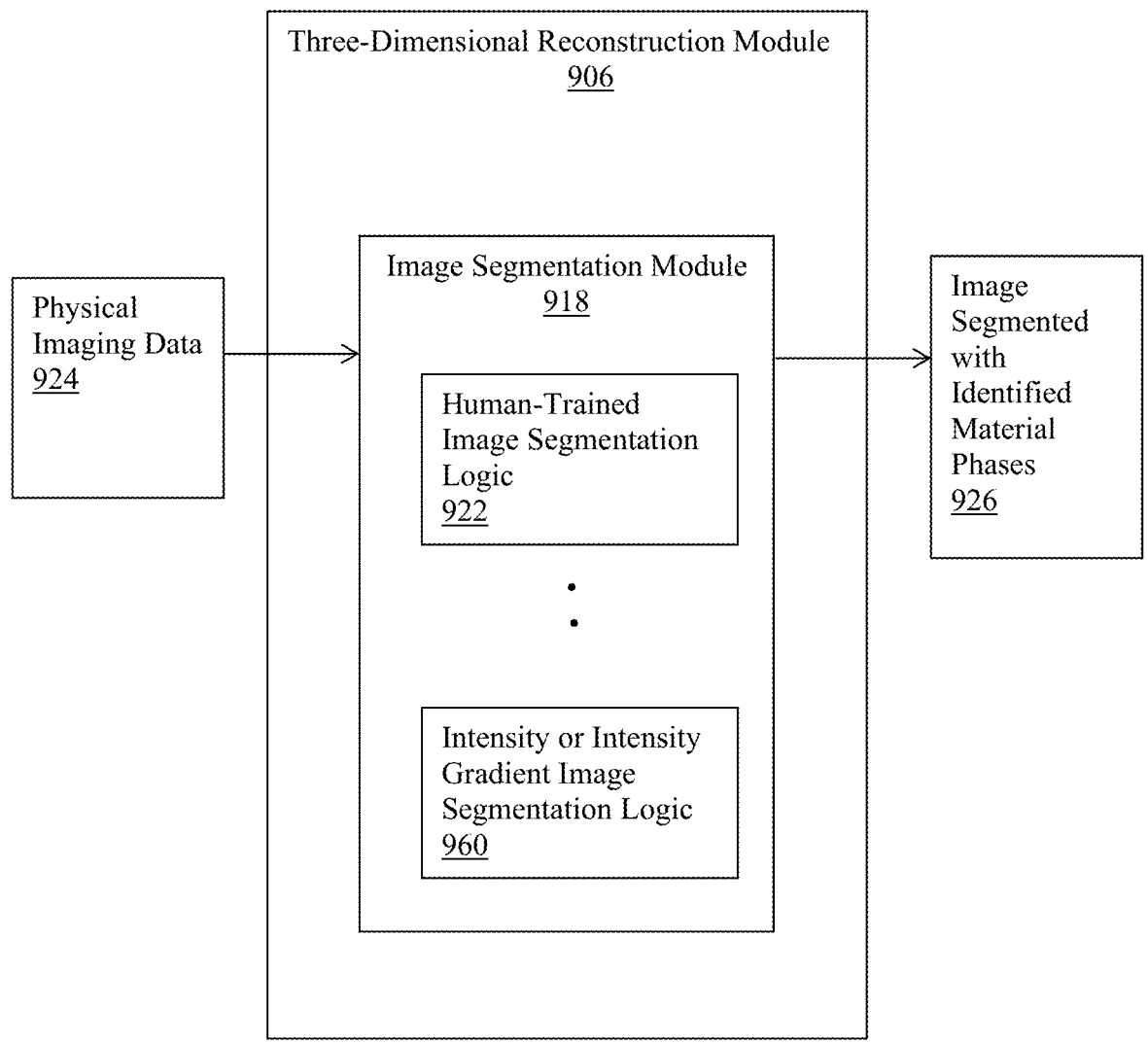
FIG. 9 is a schematic block diagram of a three-dimensional reconstruction module in accordance with an embodiment of the invention.

FIG. 9 is a schematic block diagram of a three-dimensional reconstruction module 906 in accordance with an embodiment of the invention. The three-dimensional reconstruction module 906 comprises an image segmentation module 918 configured to perform image segmentation of physical imaging data 924 and to identify material phases 926 in the physical imaging data. In accordance with an embodiment of the invention, image segmentation can be performed using artificial intelligence-based image segmentation, such as, for example, using a human-trained image segmentation logic module 922 to recognize image features. Alternatively, or in addition, the image segmentation module 918 can perform an intensity-based image segmentation or a gradient-based image segmentation using logic 960. In an intensity-based image segmentation, for example, material phases are assigned to regions of an image based on whether the intensity exceeds, or does not exceed, a given grayscale threshold intensity value. In a gradient-based image segmentation, for example, material phases are assigned to the regions in the image based on determining locations of changes in gradient of grayscale intensity values in the image. As an alternative, other gradient-based techniques, such as local threshold, top hat, watershed, or other segmentation techniques can be used. When using a human-trained image segmentation logic module 922 to recognize image features, the module 922 can function, as shown, in more detail with reference to a human-trained image segmentation logic module 1222, as shown in the block diagram of FIG. 12, and as described further below.

Figure 10:
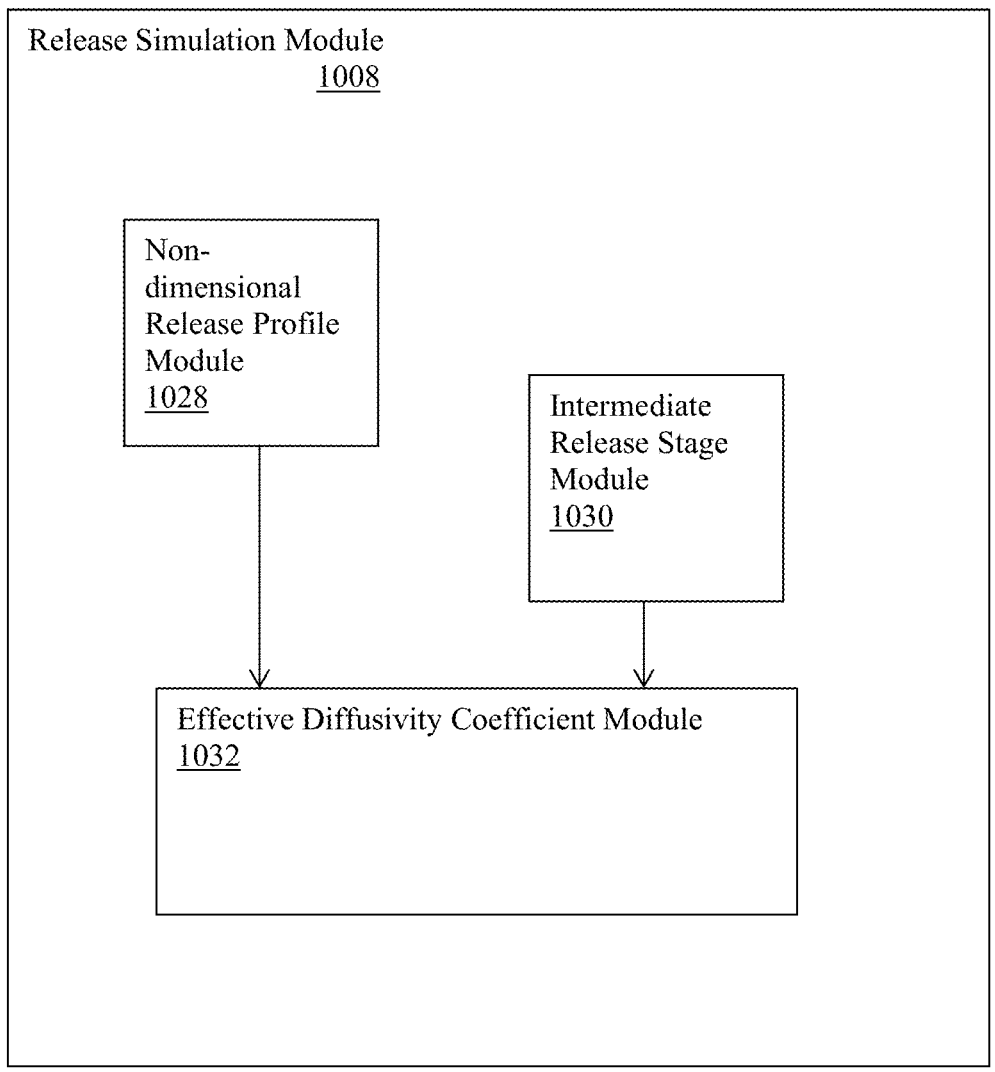
FIG. 10 is a schematic block diagram of a release simulation module in accordance with an embodiment of the invention.

FIG. 10 is a schematic block diagram of a release simulation module 1008 in accordance with an embodiment of the invention. The release simulation module 1008 further comprises a non-dimensional release profile module 1028 configured to perform a percolation-based simulation to determine a non-dimensional release profile. The non-dimensional release profile is comprised of the amount of a pharmaceutical ingredient released at each simulated, non-dimensional step of a layer-by-layer release of the pharmaceutical ingredient proceeding from an exterior surface of the release system to an interior surface of the release system. The release simulation module 1008 further comprises an intermediate release stage module 1030 configured to perform a percolation-based simulation to determine an intermediate release stage microstructure for each simulated, non-dimensional step of a layer-by-layer release of the pharmaceutical ingredient from the release system, the layer by layer release proceeding from an exterior surface of the release system to an interior surface of the release system. The release simulation module further comprises an effective diffusivity coefficient module 1032 configured to use the determined intermediate release stage microstructures to determine an effective diffusivity coefficient.

Figure 11:
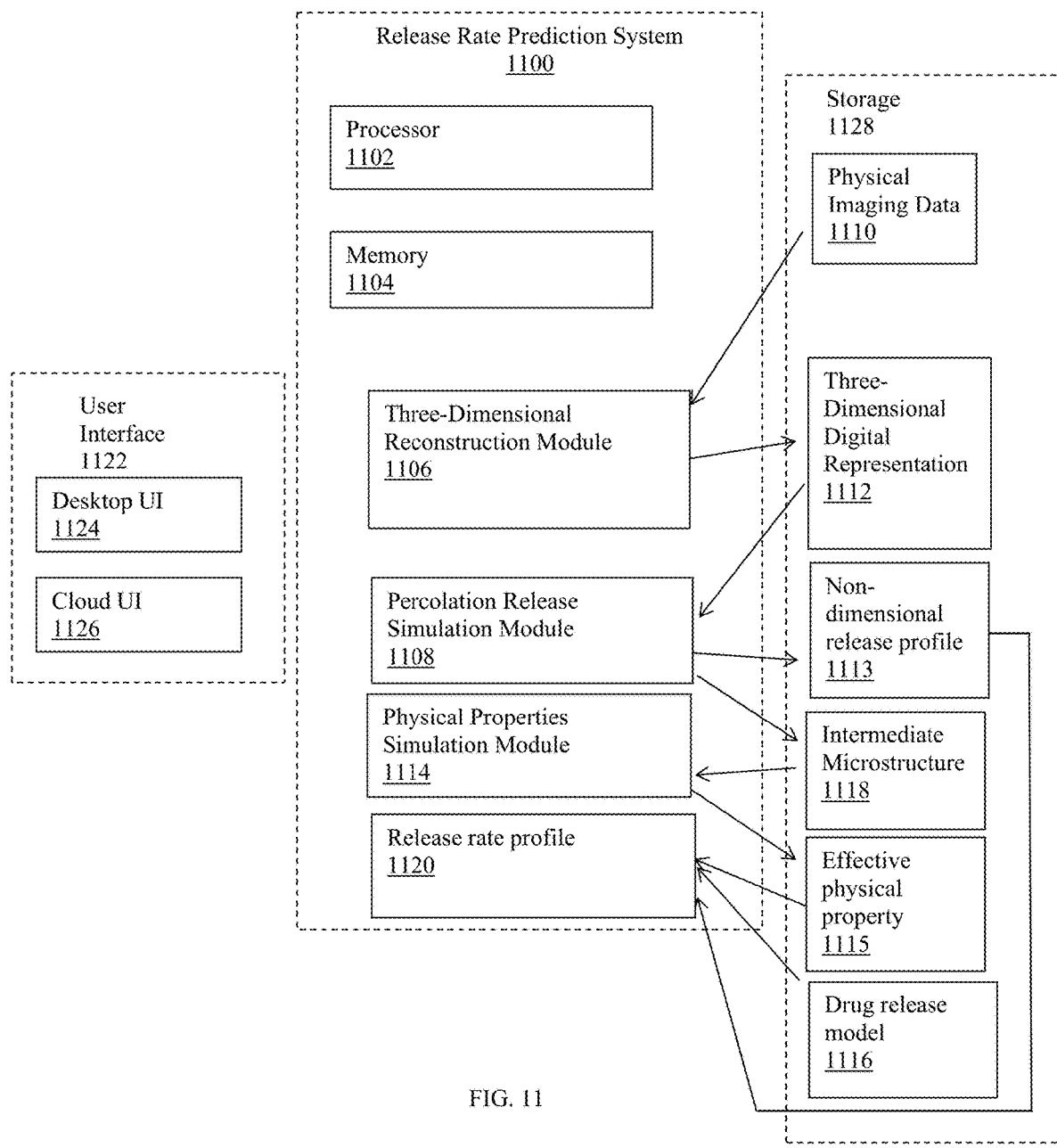
FIG. 11 is a detailed schematic block diagram of a release rate prediction system in accordance with an embodiment of the invention.

FIG. 11 is a detailed schematic block diagram of a release rate prediction system (712, see FIG. 7) in accordance with an embodiment of the invention. The computer system 1100 predicts a release rate of a pharmaceutical ingredient from a release system, and comprises a processor 1102 and a memory 1104 with computer code instructions stored thereon. The processor 1102 and the memory 1104, with the computer code instructions, are configured to implement a three-dimensional digital release system reconstruction module 1106 and release simulation modules 1108 and 1114. The three-dimensional reconstruction module 1106 is configured to construct a three-dimensional digital representation 1112 of the release system based on the physical imaging data 1110 of a sample of the release system. The three-dimensional digital representation (1112) satisfies a representative elementary volume evaluation of the pharmaceutical ingredient in the release system. The percolation release simulation module 1108 is configured to computationally simulate a non-dimensional release profile comprising an amount of the pharmaceutical ingredient released at each simulated, non-dimensional step of a layer-by-layer release of the pharmaceutical ingredient proceeding from an exterior surface of the release system to an interior surface of the release system. Module 1108 also produces microstructures from intermediate release stages (1118). The microstructures in intermediate release stages are used in the physical properties simulation module (1114) to compute physical properties, such as effective diffusivity which corresponds to the current release stage. The non-dimensional release profile (1113), effective diffusivity (1115), and a drug release model from an infinitesimal drug layer (1116) are then used to derive the release rate profile (1120). Intermediate and final output are stored on storage device (1128). Both the release prediction computer system (1100) and storage (1128) can be accessed, managed, and visualized with the user interface module (1122). The user interface can be a Cloud UI (1126) in accordance with an embodiment of the invention, and/or a desktop UI (1124) and/or.

In accordance with an embodiment of the invention, the three-dimensional reconstruction of the digital release system requires image segmentation, which can be performed using artificial intelligence-based image segmentation, such as, for example, using a human-trained image segmentation logic module to recognize image features. When using a human-trained image segmentation logic module to recognize image features, it can function, as shown in more detail with reference to a human-trained image segmentation logic module 1222 in the block diagram of FIG. 12, in accordance with an embodiment of the invention. The module 1222 takes, as its input, greyscale values of imaging data 1234, for example, which can, for example, be MicroCT images or other physical imaging data taught herein. A training image is selected 1236, a training area is selected 1238, and then an iterative process of phase seeding 1240 and training 1242 is performed. The final result is applied to an image slice 1244 or other portion of the image, and the dataset is then segmented 1246. The resulting material phases 1248 can, for example, be phases such as porosity, polymer excipient, amorphous active pharmaceutical ingredient (API), and crystalline API, or other material phases. In accordance to an embodiment of this invention, machine learning is implemented on a cloud computing platform to support the Human-trained Image Segmentation Logic Module.

Although embodiments are described herein as related to an extended release drug design, it will be appreciated that embodiments according to the invention can be applied to a variety of drugs and medical devices. In addition, embodiments in accordance with the invention can also be used outside pharmaceutical applications, such as in the fields of fluid filtration, additive reinforced material, and, more generally, applications involving predicting mass transport rates using images.

In an embodiment according to the invention, processes described as being implemented by one processor may be implemented by component processors, and/or a cluster of processors configured to perform the described processes which may be performed in parallel synchronously or asynchronously. Such component processors may be implemented on a single machine, on multiple different machines, in a distributed fashion in a network, or as program module components implemented on any of the foregoing.

Figure 13:
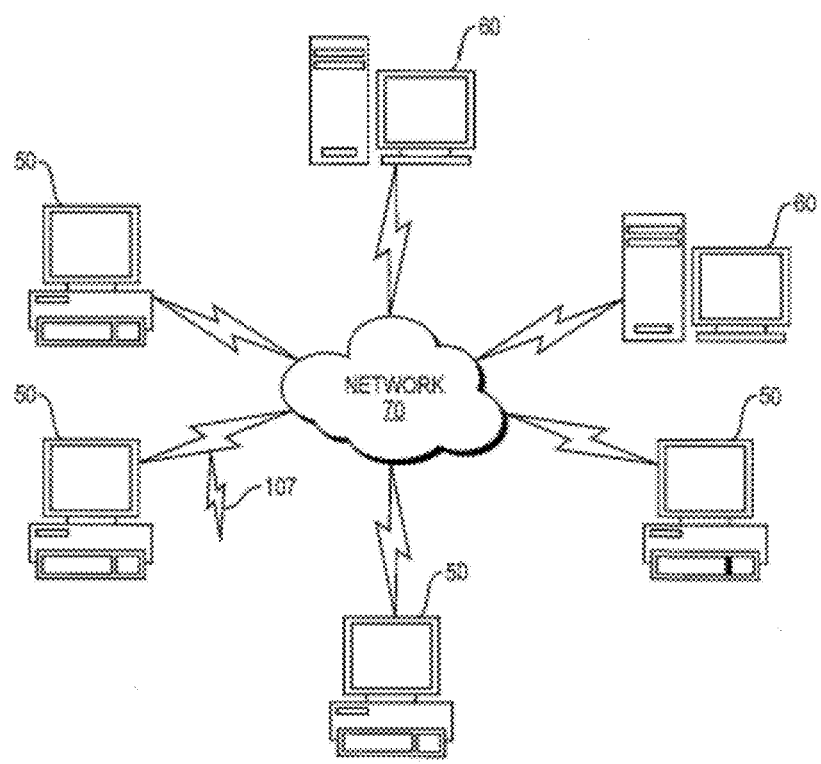
FIG. 13 illustrates a computer network, or a similar digital processing environment, in which embodiments of the present invention may be implemented.

FIG. 13 illustrates a computer network or similar digital processing environment in which embodiments of the present invention may be implemented. Client computer(s)/device(s) 50 and server computer(s) 60 provide processing, storage, and input/output devices executing application programs and the like. The client computer(s)/device(s) 50 can also be linked through communications network 70 to other computing devices, including other client devices/processes 50 and server computer(s) 60. The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 14:
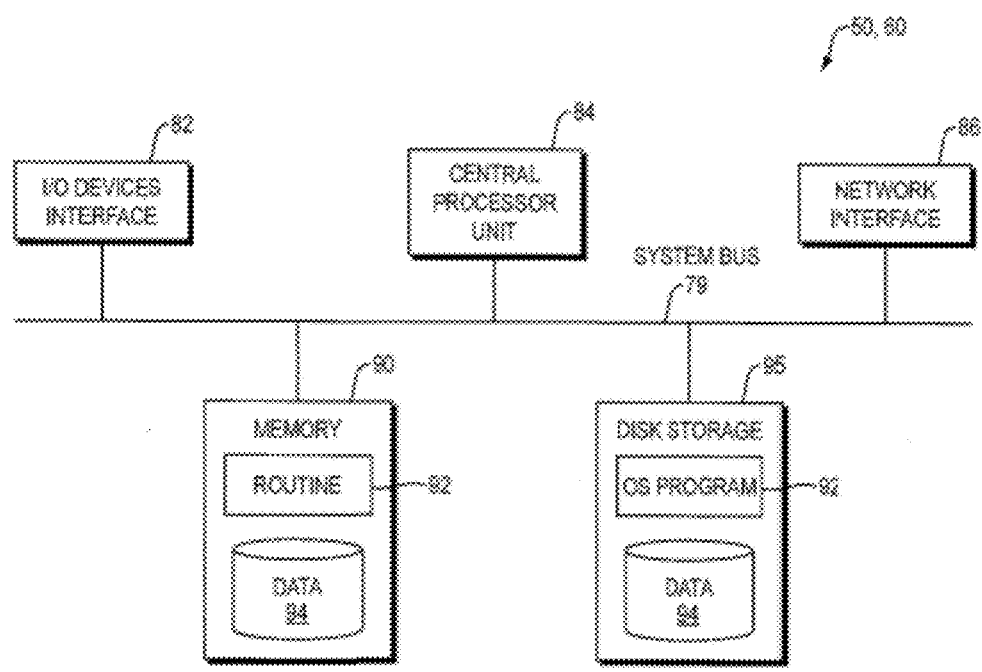
FIG. 14 is a diagram of an example internal structure of a computer (e.g., client processor/device or server computers) in the computer system of FIG. 13.

FIG. 14 is a diagram of an example internal structure of a computer (e.g., client processor/device 50 or server computers 60) in the computer system of FIG. 13. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) and enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to other various devices attached to a network (e.g., network 70 of FIG. 13). Memory 90 provides volatile storage for computer software instructions 92 and data 94 used to implement an embodiment of the present invention (e.g., release rate prediction system 800, three-dimensional reconstruction module 806, release simulation module 808, image segmentation module 918, human-trained image segmentation logic 922, intensity or intensity-gradient image segmentation logic 960, human-trained image segmentation logic 1222, release simulation module 1008, non-dimensional release profile module 1028, intermediate release stage module 1030, and effective diffusivity coefficient module 1032, release rate prediction system 1100, three-dimensional reconstruction module 1106, percolation release simulation module 1108, physical simulation module 1114, detailed herein). Disk storage 95 provides non-volatile storage for the computer software instructions 92 and the data 94 used to implement an embodiment of the present invention. A central processor unit 84 is also attached to the system bus 79 and provides for the execution of computer instructions.

In one embodiment, the processor routines 92 and data 94 are a computer program product (generally referenced 92), including a non-transitory, computer-readable medium (e.g., a removable storage medium such as one or more DVD-ROMs, CD-ROMs, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals may be employed to provide at least a portion of the software instructions for the present invention routines/program 92.

In alternative embodiments, the propagated signal is an analog carrier wave or digital signal carried on the propagated medium. For example, the propagated signal may be a digitized signal propagated over a global network (e.g., the Internet), a telecommunications network, or other networks. In one embodiment, the propagated signal is a signal that is transmitted over the propagation medium over a period of time, such as the instructions for a software application sent in packets over a network over a period of milliseconds, seconds, minutes, or longer.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

REFERENCES

U.S. Pat. No. 8,637,111, Methods for modulating the release rate of a drug-coated stent, 2012
U.S. Pat. No. 8,628,568, Stent with drug coating with variable release rate, 2010
U.S. Pat. No. 8,389,044 Poly(ester amide)-based drug delivery systems with controlled release rate and morphology, 2011
U.S. Pat. No. 8,377,499, Methods of forming Poly(ester amide)-based drug delivery systems with controlled release rate and morphology
Baxter J L, Kukura J, Muzzio F J. Hydrodynamics-induced variability in the USP apparatus II dissolution test. Int J Pharm 2005; 292:17-28.
S. Brissos, M. R. Veguilla, D. Taylor, V. Balanza-Martinez, The role of long-acting injectable antipsychotics in schizophrenia: a critical appraisal, Ther. Adv. Psychopharmacology, 4(5) (2014 198-219.
Susan D'Souza, A Review of In Vitro Drug Release Test Methods for Nano-Sized Dosage Forms, Advances in Pharmaceutics Volume 2014 (2014), Article D 304757
Diez-Escudero A, Espanol M, Montufar E B, Di Pompo G, Ciapetti G, Baldini N, Ginebra M P. Focus Ion Beam/Scanning Electron Microscopy Characterization of Osteoclastic Resorption of Calcium Phosphate Substrates. Tissue Eng Part C Methods. 2017 February; 23(2):118-124. doi: 10.1089/ten.TEC.2016.0361. Epub 2017 Feb. 3.
Hill, R. (1963), "Elastic properties of reinforced solids: some theoretical principles." *Journal of the Mechanics and Physics of Solids,* 11 (5): 357-372
Fan Q, Mitchnick M, Loxley A, "The Issues and Challenges Involved in IVRT for Semi-solid Formulations", Drug Delivery Technology, 2007: 7: 62-66.
John-Bruce D. Green, Timothy Fulghum, Mark A. Nordhaus. A review of immobilized antimicrobial agents and methods for testing, Biointerphases, December 2011, Volume 6, Issue 4, pp MR13-MR28
L. Grimaldi-Bensouda, et al., Does long-acting injectable risperdone make a difference to the real life treatment of schizophrenia? Results of the cohort for the general study of Schizophrenia (CGS), Schizophrenia Research, 134 (2012) 187-194.
R. J. Landovitz, The promise and Pitfalls of long-acting injectable agents for HIV prevention, Curr. Opin. HIV AIDS, 11(1) 2016 122-128.
Daniel Markl and J. Axel Zeitler. A Review of Disintegration Mechanisms and Measurement Techniques, Pharm Res. 2017; 34(5): 890-917.
Ketan Pancholi. A review of imaging methods for measuring drug release at nanometre scale: a case for drug delivery systems. Expert Opinion on Drug Delivery. Volume 9, 2012, Issue 2.
Roberto Pisano, Antonello A. Barresi, Luigi C. Capozzi, Giorgia Novajra, Irene Oddone, and Chiara Vitale-Brovarone. Characterization of the mass transfer of lyophilized products based on X-ray micro-computed tomography images. Drying Technology, VOL. 35, No. 8., 933-938, 2017.
A. Putz, J. Jankovic, S. Zhang, D. Susac, M. Secanell, M. Sabharwal. Microscope Supported Multi-scale Modeling of PEM Fuel Cell. Presentation at 231st The Electrochemical Society Meeting, session F03: Multiscale Modeling, Simulation and Design, New Orleans, May 28-Jun. 1, 2017.
Qureshi S A, McGilveray I J. Typical variability in drug dissolution testing: Study with USP and FDA calibrator tablets and a marketed drug (glibenclamide) product. Eur J Pharm Sci 1999; 7:249-258.
J. Siepmann, R. A. Siegel, M. J. Rathbone. Fundamentals and Applications of Controlled Release Drug Delivery. Springer, 2012.
Siepmann J., Siepmann F. Modeling of diffusion controlled drug delivery. J Control Release. 2012 Jul. 20; 161(2): 351-62. doi: 10.1016/j.jconrel.2011.10.006. Epub 2011 Oct. 13.
Wang Y, Wertheim D F, Jones A S, Chang H I, Coombes A G. Micro-CT analysis of matrix-type drug delivery devices and correlation with protein release behaviour. J Pharm Sci. 2010 June; 99(6):2854-62. doi: 10.1002/jps.22027.
Dan Wu and Shawn Zhang. Microimaging Characterization and Release Prediction of Controlled Release Microspheres. 18-A-137-CRS. Controlled Release Society Annual Meeting and Exposition, New York City, N.Y., U.S.A. Jul. 22-24, 2018.
S. Zhang. Correlative focused ion beam scanning electron microscope and x-ray micro-computed tomography imaging on multi-scale drug release characterization and three-dimensional-printing manufacturing. CRS 2017 Annual Conference Poster Presentation. Poster No. 128, Jul. 16-19, 2017, Boston.
S. Zhang., DigiM Artificial Intelligence Image Processing. DigiM Technology Highlight 2017 July Issue. Jul. 29, 2017.
S. Zhang & J. Chen. DigiMedicine: FIB-SEM/MicroCT three-dimensional imaging for drug microstructure and deliverability characterization. AAPS National Biotechnology Conference 2016.
Shawn Zhang, Joseph Neilly, Aiden Zhu, Jacie Chen, Gerald Danzer. Quantitative Characterization of Crystallization in Amorphous Solid Dispersion Drug Tablets Using X-Ray Micro-Computed Tomography. Microscopy & Microanalysis 2018, Baltimore, Md., Aug. 5-9, 2018.
S. Zhang, Robert E. Klimentidis, & Patrick Barthelemy. "Micron to millimeter upscale of shale rock properties based on three-dimensional imaging and modeling". *Soci-* ety of Core Analysis 2012 Meeting, paper A080, Aberdeen, UK, Aug. 26-31, 2012.

S. Zhang, C. Zhang, G. Byrnes. Microscopic Image Based Drug Delivery System Characterization. AAPS 2016 Annual Conference, Poster #02W0900, Denver, Colo., USA, Nov. 13-17, 2017.

What is claimed is:

1. An image-based, computer-implemented method of predicting release of a pharmaceutical ingredient from a release system, the method comprising:
 constructing a three-dimensional digital representation of the release system based on physical imaging data of a sample of the release system; the three-dimensional digital representation satisfying a representative elementary volume evaluation of the pharmaceutical ingredient in the release system; and
 predicting the release by computationally simulating the release of the pharmaceutical ingredient from the release system based on (i) physical properties governing the release, (ii) the three-dimensional digital representation of the release system, and (iii) at least one of: a percolating network of porosity of the release system, and a percolating network of porosity formed as the pharmaceutical ingredient is released from the release system, wherein computationally simulating the release of the pharmaceutical ingredient from the release system comprises performing a percolation-based simulation to determine at least one of:
  a non-dimensional release profile comprising an amount of the pharmaceutical ingredient released at each simulated, non-dimensional step of a layer-by-layer release of the pharmaceutical ingredient proceeding from an exterior surface of the release system to an interior of the release system; and
  an intermediate release stage microstructure for each simulated, non-dimensional step of a layer-by-layer release of the pharmaceutical ingredient from the release system, the layer-by-layer release proceeding from the exterior surface of the release system to the interior of the release system.

2. The computer-implemented method of claim 1, wherein constructing the three-dimensional digital representation comprises, for at least one iteration:
 determining whether the three-dimensional digital representation of the release system satisfies the representative elementary volume evaluation; and
 if the three-dimensional digital representation of the release system does not satisfy the representative elementary volume evaluation, revising the three-dimensional digital representation of the release system and again determining whether the three-dimensional digital representation of the release system satisfies the representative elementary volume evaluation.

3. The computer-implemented method of claim 1, comprising constructing the three-dimensional digital representation of the release system based on three-dimensional imaging data, two-dimensional imaging data, or at least one pre-existing three-dimensional digital representation of a release system with identical or similar design.

4. The computer-implemented method of claim 1, wherein constructing the three-dimensional digital representation of the release system comprises performing image segmentation of the physical imaging data to identify material phases in the physical imaging data, wherein performing the image segmentation comprises performing at least one of: an intensity-based image segmentation, a gradient-based image segmentation and an artificial intelligence-based image segmentation.

5. The computer-implemented method of claim 4, wherein performing the artificial intelligence-based image segmentation comprises using a human-trained image segmentation logic module to recognize image features.

6. The computer-implemented method of claim 1, further comprising using the determined intermediate release stage microstructures to determine an effective diffusivity coefficient.

7. The computer-implemented method of claim 6, further comprising:
 determining concentration distribution of the pharmaceutical ingredient throughout the at least one of the percolating network of porosity of the release system and the percolating network of porosity formed as the pharmaceutical ingredient is released from the release system, based on solving flux balance with a numerical method; and
 based on the concentration distribution, determining the effective diffusivity coefficient.

8. The computer-implemented method of claim 7, comprising determining the effective diffusivity coefficient based on a direct numerical simulation employing voxels of the three-dimensional digital representation of the release system as the computation cell of the direct numerical simulation.

9. The computer-implemented method of claim 1, comprising predicting release rate of the pharmaceutical ingredient from the release system based on at least: (i) the non-dimensional release profile and (ii) an effective diffusivity coefficient.

10. The computer-implemented method of claim 1, wherein the physical imaging data includes physical imaging data obtained at a first resolution scale and physical imaging data obtained at a second resolution scale, the method comprising:
 performing a first simulation based on the physical imaging data obtained at a first resolution scale; and
 performing a second simulation based on the physical imaging data obtained at a second resolution scale, different from the first resolution scale.

11. The computer-implemented method of claim 10, wherein the first simulation comprises a percolation-based simulation based on the physical imaging data obtained at the first resolution scale; and
 wherein the second simulation comprises an effective diffusivity simulation based on the physical imaging data obtained at the second resolution scale.

12. The computer-implemented method of claim 1, wherein:
 the physical imaging data comprises images produced from at least one of: computed tomography; focused ion beam scanning electron microscopy; magnetic resonance imaging; ultrasound imaging; light microscopy; transmission electron microscopy; Raman Imaging; and atomic force microscopy;
 the release system comprises at least one of: a drug; a medical device; and biological tissue;
 the drug comprises at least one of: a tablet; a pellet; a spray-dried particle; a lyophilized solid; a microsphere; a nano-sphere; and an implant;
 the method further comprising:
 computationally simulating the release of the pharmaceutical ingredient from the release system comprises performing at least one direct numerical simulation of the physical properties governing the release by numerically solving partial differential equations governing the physical properties, the partial differential equations comprising at least one of: Second Fick's law for diffusion; Navier-Stokes equations for pressure gradient or flux driven flow; Ohm's law for electrical conductivity; and Fourier's law for thermal conductivity;

wherein computationally simulating the release of the pharmaceutical ingredient from the release system comprises performing at least one of: a finite volume numerical simulation, a finite difference numerical simulation, a finite element numerical simulation, and a Lattice Boltzmann numerical simulation;

employing voxels of the three-dimensional digital representation of the release system as a smallest computation cell in computationally simulating the release of the pharmaceutical ingredient from the release system, each voxel of the voxels of the three-dimensional digital representation of the release system comprising an integer value representing material phase information; and wherein the material phase information comprises: at least one matrix phase; at least one pharmaceutical ingredient phase, and optionally at least one porosity phase.

13. The computer-implemented method of claim 1, comprising predicting the release rate of the pharmaceutical ingredient from the release system based on the three-dimensional digital representation of the release system, at least one physical property of the pharmaceutical ingredient, and an established release model.

14. The computer-implemented method of claim 13, wherein the at least one physical property of the pharmaceutical ingredient comprises at least one of: an effective diffusivity coefficient, and a permeability.

15. The computer-implemented method of claim 13, wherein the established release model comprises at least one of: a Higuchi thin plate model, a Higuchi cylinder model, and a Higuchi sphere model.

16. The computer-implemented method of claim 1, wherein the physical properties governing the release comprise at least one of: a diffusion coefficient of a solute in a solvent, a concentration of the solute in the solvent, a mass flux of the pharmaceutical ingredient, a geometry of the sample of the release system, a loading of the pharmaceutical ingredient, a solubility of the pharmaceutical ingredient, a degradation profile of a solid non-drug material phase, and other relevant physical properties such as an electrical conductivity, a thermal conductivity, and a pressure gradient.

17. A computer system for predicting release of a pharmaceutical ingredient from a release system, the computer system comprising:
a processor; and
a memory with computer code instructions stored thereon, the processor and the memory, with the computer code instructions being configured to implement:
a three-dimensional reconstruction module, the three-dimensional reconstruction module being configured to construct a three-dimensional digital representation of the release system based on physical imaging data of a sample of the release system, the three-dimensional digital representation satisfying a representative elementary volume evaluation of the pharmaceutical ingredient in the release system; and
a release simulation module configured to predict the release by computationally simulating the release of the pharmaceutical ingredient from the release system based on (i) physical properties governing the release, (ii) the three-dimensional digital representation of the release system, and (iii) at least one of: a percolating network of porosity of the release system, and a percolating network of porosity formed as the pharmaceutical ingredient is released from the release system, wherein computationally simulating the release of the pharmaceutical ingredient from the release system comprises performing a percolation-based simulation to determine at least one of:
a non-dimensional release profile comprising an amount of the pharmaceutical ingredient released at each simulated, non-dimensional step of a layer-by-layer release of the pharmaceutical ingredient proceeding from an exterior surface of the release system to an interior of the release system; and
an intermediate release stage microstructure for each simulated, non-dimensional step of a layer-by-layer release of the pharmaceutical ingredient from the release system, the layer-by-layer release proceeding from the exterior surface of the release system to the interior of the release system.

18. The computer system of claim 17, wherein the release simulation module further comprises:
an effective diffusivity coefficient module configured to use the determined intermediate release stage microstructures to determine an effective diffusivity coefficient;
and wherein the release simulation module is further configured to predict a release rate based on at least: (i) the non-dimensional release profile and (ii) the effective diffusivity coefficient.

19. The computer system of claim 17, wherein the release simulation module is further configured to:
perform a first simulation based on physical imaging data obtained at a first resolution scale; and
perform a second simulation based on physical imaging data obtained at a second resolution scale, different from the first resolution scale.

20. The computer system of claim 19, wherein the first simulation comprises a percolation-based simulation based on the physical imaging data obtained at the first resolution scale; and
wherein the second simulation comprises an effective diffusivity simulation based on the physical imaging data obtained at the second resolution scale, and comprises an integration of the physical imaging data at multiple resolutions iteratively.

21. A non-transitory, computer-readable medium configured to store instructions for predicting release of a pharmaceutical ingredient from a release system, the instructions, when loaded and executed by a processor, cause the processor to predict the release of the pharmaceutical ingredient from the release system by:
constructing a three-dimensional digital representation of the release system based on physical imaging data of a sample of the release system, the three-dimensional digital representation satisfying a representative elementary volume evaluation of the pharmaceutical ingredient in the release system; and
predicting the release by computationally simulating the release of the pharmaceutical ingredient from the release system based on (i) physical properties governing the release, (ii) the three-dimensional digital representation of the release system, and (iii) at least one of: a percolating network of porosity of the release system, and a percolating network of porosity formed as the pharmaceutical ingredient is released from the release system, wherein computationally simulating the release of the pharmaceutical ingredient from the release system comprises performing a percolation-based simulation to determine at least one of:

a non-dimensional release profile comprising an amount of the pharmaceutical ingredient released at each simulated, non-dimensional step of a layer-by-layer release of the pharmaceutical ingredient proceeding from an exterior surface of the release system to an interior of the release system; and an intermediate release stage microstructure for each simulated, non-dimensional step of a layer-by-layer release of the pharmaceutical ingredient from the release system, the layer-by-layer release proceeding from the exterior surface of the release system to the interior of the release system.

* * * * *